United States Patent
Choi et al.

(10) Patent No.: US 9,415,106 B2
(45) Date of Patent: Aug. 16, 2016

(54) α-FORM ZINC-PHTHALOCYANINE NANOWIRES HAVING ENHANCED WATER SOLUBILITY AND WATER DISPERSIBILITY, COMPOSITE OF AN α-FORM ZINC-PHTHALOCYANINE NANOWIRE/PHENOTHIAZINE, AND METHOD FOR PREPARING SAME

(75) Inventors: Hee Cheul Choi, Gyeongsangbuk-do (KR); Hye Kyung Moon, Pusan (KR); Sang Ho Lee, Pusan (KR)

(73) Assignee: POHANG UNIVERSITY OF SCIENCE AND TECHNOLOGY INDUSTRY ACADEMY COOPERATION CORPS, Gyeongsangbuk-Do (KR)

( * ) Notice: Subject to any disclaimer, the term of this patent is extended or adjusted under 35 U.S.C. 154(b) by 0 days.

(21) Appl. No.: 14/347,603

(22) PCT Filed: Aug. 30, 2012

(86) PCT No.: PCT/KR2012/006939
§ 371 (c)(1),
(2), (4) Date: Aug. 12, 2014

(87) PCT Pub. No.: WO2013/048022
PCT Pub. Date: Apr. 4, 2013

(65) Prior Publication Data
US 2014/0371192 A1 Dec. 18, 2014

(30) Foreign Application Priority Data
Sep. 26, 2011 (KR) .................. 10-2011-0097092
Aug. 30, 2012 (KR) .................. 10-2012-0095442

(51) Int. Cl.
| | | |
|---|---|---|
| C07D 487/22 | (2006.01) | |
| A61K 41/00 | (2006.01) | |
| A61K 47/48 | (2006.01) | |
| A61K 49/00 | (2006.01) | |
| A61K 9/00 | (2006.01) | |
| A61K 31/5415 | (2006.01) | |
| A61K 31/555 | (2006.01) | |
| B82Y 5/00 | (2011.01) | |
| B82Y 15/00 | (2011.01) | |

(52) U.S. Cl.
CPC ........... *A61K 41/0071* (2013.01); *A61K 9/0092* (2013.01); *A61K 31/5415* (2013.01); *A61K 31/555* (2013.01); *A61K 47/48884* (2013.01); *A61K 49/0036* (2013.01); *A61K 49/0093* (2013.01); *C07D 487/22* (2013.01); *B82Y 5/00* (2013.01); *B82Y 15/00* (2013.01); *Y10T 428/298* (2015.01)

(58) Field of Classification Search
CPC .................................................. C07D 487/22
See application file for complete search history.

(56) References Cited

U.S. PATENT DOCUMENTS

| 2010/0076108 A1 | 3/2010 | Miyashita et al. |
| 2010/0108972 A1 | 5/2010 | Zhao et al. |

FOREIGN PATENT DOCUMENTS

| KR | 10-2010-0016588 | 2/2010 |
| KR | 10-2010-0049824 | 5/2010 |
| KR | 10-2010-0051163 | 5/2010 |

OTHER PUBLICATIONS

Choi, Yongdoo et al., "Cancer Imaging and Photodynamic Therapy Using Photosensitizers", Polymer Science and Technology, Apr. 30, 2008, vol. 19, No. 2, pp. 138-145.
Josefsen, Leanne B. et al., "Photodynamic Therapy and the Development of Metal-Based Photosensitisers", Metal-Based Drugs, Sep. 11, 2008, vol. 2008, 24 pages.
Owens, John Wesley et al., "Photophysical properties of porphyrins, phthalocyanines, and benzochlorins", Inorganica Chimica Acta, Oct. 1, 1998, vol. 279, pp. 226-231.
O'Connor, Aisling E. O. et al., "Porphyrin and nonporphyrin photosensitizers in oncology: preclinical and clinical advances in photodynamic therapy", Photochemistry and Photobiology, Aug. 3, 2009, pp. 1053-1074.
Moon, Hye Kyung et al., "Significant increase in the water dispersibility of zinc phthalocyanine nanowires and applications in cancer phototherapy", NPG Asia Materials, Apr. 13, 2012, vol. 4, 8 pages.
Oleinick, Nancy L. et al., "The role of apoptosis in response to photodynamic therapy: what, where, why, and how", Photochemical and Photobiological Sciences, Jan. 2002, vol. 1, pp. 1-21.

*Primary Examiner* — Brian McDowell
(74) *Attorney, Agent, or Firm* — Pillsbury Winthrop Shaw Pittman LLP

(57) ABSTRACT

The present invention relates to alpha-form zinc-phthalocyanine nanowires (ZnPc NWs) having enhanced water solubility and water dispersibility, to a composite of an alpha-form zinc-phthalocyanine nanowire/phenothiazine, to a method for preparing same, and to a photosensitizer including same or a pharmaceutical composition including same for preventing or treating cancers. Since the alpha-form zinc-phthalocyanine nanowires or the composite of alpha-form zinc-phthalocyanine nanowire/phenothiazine according to the present invention exhibit dual traits, i.e., photothermal and photodynamic traits in single molecules, they are very useful for the development of a multifunctional molecular system and can also be usefully applied to light therapy of cancers due to their good light therapeutic effects. Also, the composite of alpha-form zinc-phthalocyanine nanowire/phenothiazine itself can exhibit fluorescence to facilitate the introduction of an imaging system, so that diagnosis and treatment can be simultaneously performed using a single substance.

4 Claims, 22 Drawing Sheets

α-FORM ZINC-PHTHALOCYANINE NANOWIRES HAVING ENHANCED WATER SOLUBILITY AND WATER DISPERSIBILITY, COMPOSITE OF AN α-FORM ZINC-PHTHALOCYANINE NANOWIRE/PHENOTHIAZINE, AND METHOD FOR PREPARING SAME

CROSS REFERENCE TO RELATED APPLICATIONS

This application is a national stage entry of International Application No. PCT/KR2012/006939 filed on Aug. 30, 2012 which claims priority to Korean Patent Application No. 10-2011-0097092 filed on Sep. 26, 2011 and Korean Patent Application No. 10-2011-0095442 filed on Aug. 30, 2012, the entire contents of which are herein incorporated by reference.

TECHNICAL FIELD

The present invention relates to α-form zinc-phthalocyanine nanowires (ZnPc NWs) with increased water solubility and water dispersibility, a composite of α-form zinc-phthalocyanine nanowire/phenothiazine, a method for preparing the same, a photosensitizer comprising the same, and a pharmaceutical composition comprising the same for preventing or treating cancers.

BACKGROUND ART

Photodynamic therapy (PDT) is an advanced modality for the treatment of malignant tumors as it is widely used for clinical cancer treatments. This photodynamic therapy selectively destroys neoplastic lesions using cytotoxic reactive oxygen species (ROS) generated by light activation of the photosensitizer. One of the crucial factors determining the photodynamic therapy efficacy is the photochemical and photophysical properties of the photosensitizer.

The photosensitizers are classified into the following four main classes: porphyrin derivatives, chlorine, porphycenes, and phthalocyanines (Pcs). Among these, metallo-phthalocyanine (MPc) has attracted considerable interest, having a photodynamic (PD) property that can be readily tuned by the type of central metal ion and the functional groups introduced as a phthalocyanine (Pc) ring substituent. Zinc phthalocyanine (ZnPc) is known to exhibit a high photodynamic effect as it possesses a diamagnetic Zn(II) central metal ion whose d shell is fully occupied, by which the yield of triplet excited state with long lifetime essential for the generation of ROS becomes high. Moreover, ZnPc has a large absorption cross-section of light at the tissue-penetrating spectral range of 650-900 nm.

The biggest problem for most photosensitizers, including ZnPc, for the photodynamic therapy is the low physiological acceptance level due to their high hydrophobic characteristics responsible for the poor solubility in a bodily fluid. To overcome this problem, ZnPc derivatives, such as tetrasulfonated ZnPc (ZnPcS$_4$), [1,2,3,4-tetrakis(α/β-D-galactopyranos-6-yl)-phthalocyaninato]zinc, tetra- and octa-triethyleneoxysulfonyl substituted ZnPc, have been designed to increase the water solubility. Moreover, various delivery vehicles including liposome, emulsion, and nanoparticles have also been developed to transport water-insoluble photosensitizers to targets.

However, these approaches require multiple and complex chemical functionalization steps, during which the photoactivity could be reduced by destroying the original electronic conjugation system of the photosensitizer. Another challenging issue is the realization of a photosensitizer that exhibits both photodynamic and photothermal effects simultaneously to conduct dual synergistic phototherapy, which is rarely found from a single photosensitizer.

Moreover, in the photodynamic therapy, a fluorescence imaging system is used to accurately determine the location of the photosensitizer in the body and the concentration of the photosensitizer accumulated in target cells, and thus it is possible to accurately treat cancer cells in a local area. Among various photosensitizers, zinc-phthalocyanine nanowires can absorb light at long wavelengths and generate much more reactive oxygen species due to the presence of zinc atoms, but the introduction into the fluorescence imaging system is not easy due to the absence of fluorescence.

Therefore, there is a need to develop a composite in which a material that exhibits fluorescence is introduced to overcome these drawbacks.

DISCLOSURE

Technical Problem

Accordingly, the present inventors have found that when ZnPc powder grows into one-dimensional nanowires (NWs), the water solubility and water dispersibility significantly increases, even without any special functional groups introduced, found that α-form ZnPc nanowires exhibit both photodynamic and photothermal effects, which are known to be absent from ZnPc powder, upon irradiation with near infrared (NIR, λ=808 nm) laser, and found that when a composite is prepared by introducing phenothiazine molecules that exhibit fluorescence into these α-form ZnPc nanowires, the composite itself exhibits fluorescence, which thus can be easily introduced into an imaging system, thus completing the present invention.

Accordingly, the present invention aims at providing α-form zinc-phthalocyanine nanowires (ZnPc NWs) with increased water solubility and water dispersibility, a composite of α-form zinc-phthalocyanine nanowire/phenothiazine, and a method for preparing the same.

Moreover, the present invention aims at providing a photosensitizer comprising α-form zinc-phthalocyanine nanowires (ZnPc NWs) or a composite of α-form zinc-phthalocyanine nanowire/phenothiazine.

Furthermore, the present invention aims at providing a pharmaceutical composition for preventing or treating cancers, comprising α-form zinc-phthalocyanine nanowires (ZnPc NWs) or a composite of α-form zinc-phthalocyanine nanowire/phenothiazine as an active ingredient.

Technical Solution

The present invention provides α-form zinc-phthalocyanine nanowires with increased water solubility and water dispersibility, represented by the following Formula 1:

[Formula 1]

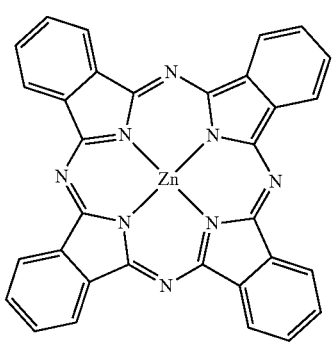

-continued

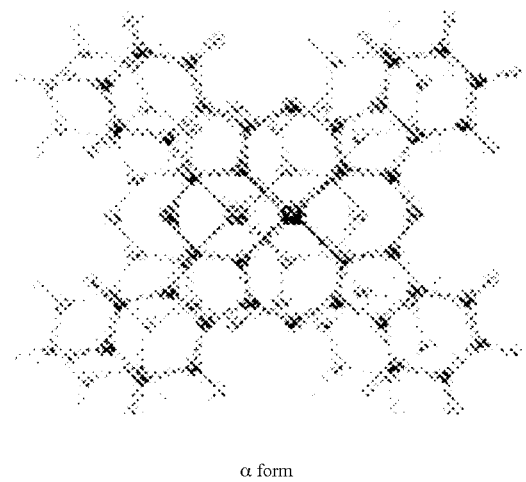

α form

The α-form zinc-phthalocyanine nanowires according to the present invention are obtained by vaporization-condensation-recrystallization (VCR). Specifically, the α-form zinc-phthalocyanine nanowires may be obtained by condensing and recrystallizing vapors, vaporized by heating raw zinc-phthalocyanine (e.g., in the form of powder) at 500° C. or higher, preferably at 550° C. or higher, for example, at 500 to 1,000° C., preferably at 550 to 800° C., more preferably at 550 to 650° C., on a substrate at a lower temperature than the heating temperature, for example, at 300° C. or lower, preferably at 200° C. or lower, more preferably at 180° C. or lower, such as at room temperature to 300° C., at room temperature to 200° C., or at room temperature to 180° C. such that zinc-phthalocyanine is grown in the form of nanowires on the substrate. The thus obtained α-form zinc-phthalocyanine nanowires may have a diameter of about 50 to 100 nm and a length of about 1 to 10 μm.

Moreover, unlike the existing zinc-phthalocyanine powder, the α-form zinc-phthalocyanine nanowires have excellent solubility and dispersibility in water and thus exhibit significantly increased stability in an aqueous solution (i.e., the stability is maintained in an aqueous solution for more than 3 months). The water solubility of the α-form zinc-phthalocyanine nanowires may be further improved by agitation such as sonication. As such, the solubility and dispersibility in water of the thus obtained α-form zinc-phthalocyanine nanowires can be up to 140 mg/L at room temperature.

Furthermore, the present invention provides a composite of α-form zinc-phthalocyanine nanowire represented by the above Formula 1 and phenothiazine.

The composite of α-form zinc-phthalocyanine nanowire/phenothiazine, in which phenothiazine molecules that exhibit fluorescence are introduced, exhibits fluorescence and thus facilitates the introduction into the imaging system, and thus the diagnosis and treatment can be achieved at the same time using a single substance.

Moreover, the present invention provides a method for preparing α-form zinc-phthalocyanine nanowires, the method comprising the steps of:

(a) generating zinc-phthalocyanine (ZnPc) vapor by vaporizing zinc-phthalocyanine by heating at 500 to 1,000° C. under an inert gas atmosphere; and (b) obtaining the α-form zinc-phthalocyanine nanowires represented by the above Formula 1 by condensing and recrystallizing the zinc-phthalocyanine vapor generated in step (a) at room temperature to 300° C. under an inert gas atmosphere.

Furthermore, the present invention provides a method for preparing a composite of α-form zinc-phthalocyanine nanowire/phenothiazine, the method comprising the steps of:

(a') generating zinc-phthalocyanine (ZnPc) and phenothiazine vapors by vaporizing zinc-phthalocyanine and phenothiazine by heating at 500 to 1,000° C. under an inert gas atmosphere; and (b') obtaining the composite of α-form zinc-phthalocyanine nanowire represented by the above Formula 1 and phenothiazine by condensing and recrystallizing the zinc-phthalocyanine and phenothiazine vapors generated in step (a') at room temperature to 300° C. under an inert gas atmosphere.

Hereinafter, the preparation method of the present invention will be described in detail step by step.

Steps (a) and (a') are to generate ZnPc vapor and/or phenothiazine vapor by vaporizing zinc-phthalocyanine and/or phenothiazine in the form of powder by heating at 500° C. or higher, preferably at 550° C. or higher, for example 500 to 1,000° C., preferably 550 to 800° C., more preferably 550 to 650° C. under an inert gas atmosphere.

Steps (b) and (b') are to condense and recrystallize the ZnPc vapor and/or phenothiazine vapor under an inert gas atmosphere on a substrate. At this time, the temperature is in a range where the ZnPc vapor and/or phenothiazine vapor generated in steps (a) and/or (a') can be collected, condensed, and recrystallized, which is lower than the heating temperature and may be 300° C. or lower, preferably 200° C. or lower, more preferably 180° C. or lower, for example room temperature to 300° C., room temperature to 200° C., or room temperature to 180° C.

The inert gas used in steps (a), (a'), (b), and (b') may be nitrogen, argon, or helium, but not limited thereto, and argon is preferably used in the present invention.

The substrate in steps (b) and (b') may be of any type that is in contact with the zinc-phthalocyanine vapor and allows nanowires to grow and may include, but not limited to, silicon, quartz, etc., for example.

Moreover, the present invention provides a photosensitizer comprising α-form zinc-phthalocyanine nanowires (ZnPc NWs) or a composite of α-form zinc-phthalocyanine nanowire represented by the above Formula 1 and phenothiazine.

The photosensitizer comprising the α-form zinc-phthalocyanine nanowires (ZnPc NWs) or the composite of α-form zinc-phthalocyanine nanowire/phenothiazine absorbs light in the near infrared range of 650 to 900 nm to generate reactive oxygen species and heat.

The phototherapy is one of the widely used clinical methods to treat cancers due to its less side effects, non-invasiveness, and high selectivity to light of a specific wavelength.

Like the photodynamic therapy (PDT) and photothermal therapy (PTT), the phototherapy requires light and photosensitizer to generate reactive oxygen species and thermal energy, respectively, and induces apoptosis.

In general, zinc phthalocyanine (ZnPc) is one of the promising photosensitizers as it has a strong absorption cross-section in the spectral range of 650 to 900 nm that guarantees maximum tissue penetration. One critical issue in using phthalocyanine (Pc) molecule, including ZnPc, is the poor water solubility of ZnPc. Therefore, in order to increase the water solubility of ZnPc, various chemical modifications inducing hydrophilicity have been widely attempted to introduce various functional groups in the ZnPc backbone.

The present inventors have found that α-form ZnPc nanowires (NWs) directly grown from ZnPc powder by vaporization-condensation-recrystallization show increased water solubility and dispersibility without any functionalization. The α-form ZnPc nanowire aqueous solution is stable for over three months without any aggregation.

Moreover, it was found that the α-form ZnPc nanowire aqueous solution exhibits highly efficient dual photodynamic and photothermal effects upon the irradiation with near infrared (NIR, λ=808 nm) laser. The dual phototherapeutic effect of α-form ZnPc nanowires was proven to enhance cytotoxicity against KB cancer cells through both in vitro and in vivo experiments.

Metallo-phthalocyanine (MPc) generates either reactive oxygen species or thermal energy upon light illumination in the near infrared region depending on the electronic configuration of the central metal. When a central metal possesses $d^0$ or $d^{10}$ (closed shell, like Zn(II)) electronic configuration, the triplet excited state has a long lifetime sufficient to be involved in the generation of ROS (photodynamic (PD) effect). On the other hand, MPc having central metals of which the d orbitals are not completely occupied (open shell, like Ni(II), Co(II), etc.) shows low PD effect, but rather exhibits fast conversion of excited electronic energy to the vibrational mode, resulting in a photothermal (PT) effect.

Because the required conditions of the electronic energy states of photosensitizers for PD and PT effects mutually conflict (i.e., the triplet excited state of the photosensitizer with long lifetime is advantageous to the PD effect but disadvantageous to the PT effect), it is difficult to realize photosensitizers that exhibit both photo effects simultaneously.

The α-form ZnPc nanowires or the composite of α-form zinc-phthalocyanine nanowire/phenothiazine according to the present invention exhibits dual PD and PT effects upon the irradiation with near infrared light. The PD activity of α-form ZnPc nanowires was proven by detecting reactive oxygen species generated upon the irradiation with near infrared (λ=808 nm) laser to the α-form ZnPc nanowires.

Accordingly, the α-form ZnPc nanowires or the composite of α-form zinc-phthalocyanine nanowire/phenothiazine according to the present invention can be effectively used as a photosensitizer.

Moreover, the present invention provides a pharmaceutical composition for preventing or treating cancers, comprising α-form zinc-phthalocyanine nanowires (ZnPc NWs) or a composite of α-form zinc-phthalocyanine nanowire/phenothiazine, represented by the above Formula 1, as an active ingredient.

Using the reactive oxygen species and heat generated upon the irradiation of infrared light (particularly, near infrared light) to the α-form zinc-phthalocyanine nanowires or the composite of α-form zinc-phthalocyanine nanowire/phenothiazine, when the α-form zinc-phthalocyanine nanowires are introduced to the tumor region and irradiated with infrared light (particularly, near infrared light), the reactive oxygen species and heat are generated to kill (eradicate) cancer cells or tissue, and thus the α-form zinc-phthalocyanine nanowires or the composite of α-form zinc-phthalocyanine nanowire/phenothiazine according to the present invention can be effectively used for the prevention or treatment of cancers.

The α-form zinc-phthalocyanine nanowires or the composite of α-form zinc-phthalocyanine nanowire/phenothiazine used in the photosensitizer or the pharmaceutical composition for preventing or treating cancers as an active ingredient may be in the form of an aqueous solution, i.e., dissolved in water. It is advantageous for the α-form zinc-phthalocyanine nanowires in the nanowire solution or the composite of α-form zinc-phthalocyanine nanowire/phenothiazine in the composite solution to have a high concentration in terms of the generation of reactive oxygen species and heat, and the concentration may be 60 mg/L or higher, preferably 80 mg/L or higher, more preferably 100 mg/L or higher, for example, 60 to 140 mg/L, 80 to 140 mg/L, 100 to 140 mg/L, or 110 to 130 mg/L.

Examples of cancers that can be treated with the α-form zinc-phthalocyanine nanowires or the composite of α-form zinc-phthalocyanine nanowire/phenothiazine according to the present invention may include all types of solid cancers, particularly epithelial cancers caused by malignant transformation of epithelial tissues such as skin, membranes, etc., and may be at least one selected from the group consisting of oral squamous cell carcinoma, skin cancer, breast cancer, stomach cancer, ovarian cancer, cervical cancer, liver cancer, lung cancer, prostate cancer, kidney cancer, and thyroid cancer.

The pharmaceutical composition of the present invention may comprise at least one known active ingredient having an anticancer effect in combination with the α-form zinc-phthalocyanine nanowires or the composite of α-form zinc-phthalocyanine nanowire/phenothiazine.

For administration, the pharmaceutical composition of the present invention may further comprise at least one pharmaceutically acceptable carrier in addition to the above active ingredients. Examples of the pharmaceutically acceptable carrier include saline, sterile water, Ringer's solution, buffered saline, dextrose solution, maltodextrin solution, glycerol, ethanol and combinations thereof. If necessary, other general additives, such as antioxidant, buffer solution, antibacterial agent, etc., may be added to the composition. Moreover, the pharmaceutical composition of the present invention may be formulated into injections such as aqueous solution, suspension, emulsion, etc., tablets, capsules, granule or pills by adding diluent, surfactant, binder and lubricant. Furthermore, the pharmaceutical composition of the present invention may be formulated by suitable methods in the art or methods described in Remington's Pharmaceutical Science (latest edition), Mack Publishing Company, Easton Pa., depending on the disease and/or ingredients.

The pharmaceutical composition of the present invention may be administered orally or parenterally (e.g., intratumorally, intravascularly, intravenously, subcutaneously, intraperitoneally, or topically) at a dose depending on various factors including the patient's weight, age, gender, state of health, diet, administration time, administration route, excretion rate, severity of disease, etc. The daily dose of the α-form zinc-phthalocyanine nanowires may be 0.00001 to 1 mg/mm$^3$ (tumor volume), preferably 0.0001 to 0.1 mg/mm$^3$ (tumor volume), but not limited thereto.

For the prevention or treatment of cancers, the pharmaceutical composition of the present invention may be used alone or in combination with other therapies, including surgical therapy, hormonal therapy, drug therapy, and therapies using biological response modifiers.

Advantageous Effects

The α-form zinc-phthalocyanine nanowires or the composite of α-form zinc-phthalocyanine nanowire/phenothiazine according to the present invention can exhibit dual photothermal and photodynamic effects from a single molecule, which have significant advantages for the development of multifunctional molecular systems and have superior phototherapeutic effects, and thus can be effectively used for cancer phototherapy. Moreover, the composite of α-form zinc-phthalocyanine nanowire/phenothiazine exhibits fluorescence and thus facilitates the introduction into the imaging system, and thus the diagnosis and treatment can be achieved at the same time using a single substance.

Figure 4:
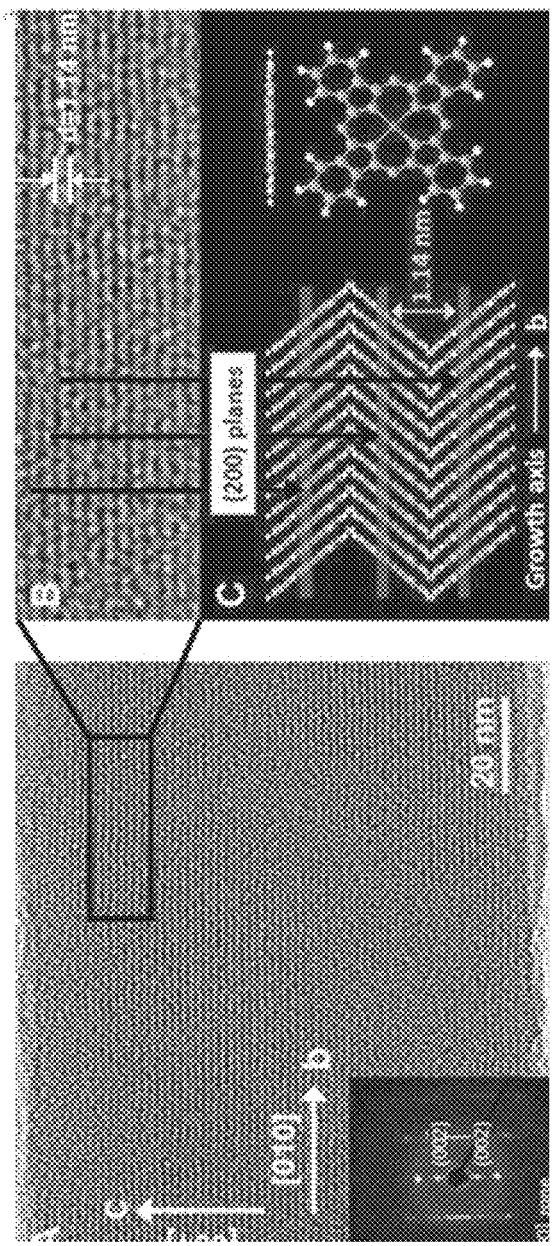

Part A of FIG. 4 shows a high resolution TEM image of an isolated single α-form ZnPc nanowire grown along the [010] direction (the insert shows the SAED pattern of the ZnPc nanowire grown along the [100] direction), part B of FIG. 4 shows an enlarged view of the yellow box of part A (interplanar spacing of lattice image: 1.14 nm), part C of FIG. 4 schematically shows the crystal structure of α-form ZnPc nanowire in projection along the a-axis, in which the zinc planes are highlighted in red, corresponding to the array of Zn(II) ion in α-form nanowire in the left, and the molecular structure of ZnPc is shown in the right).

Figure 5:
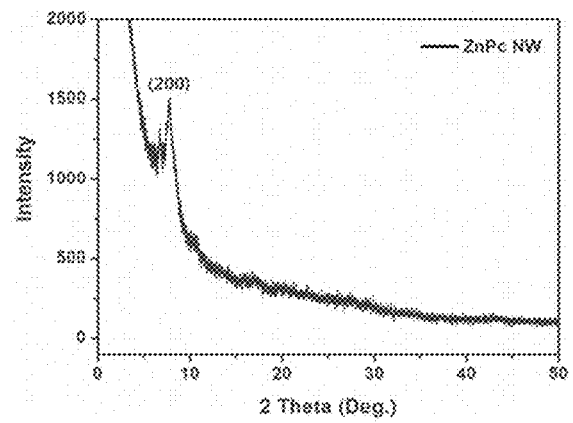

FIG. 5 shows XRD patterns of α-form ZnPc nanowires grown on Si(100) substrate.

Figure 6:
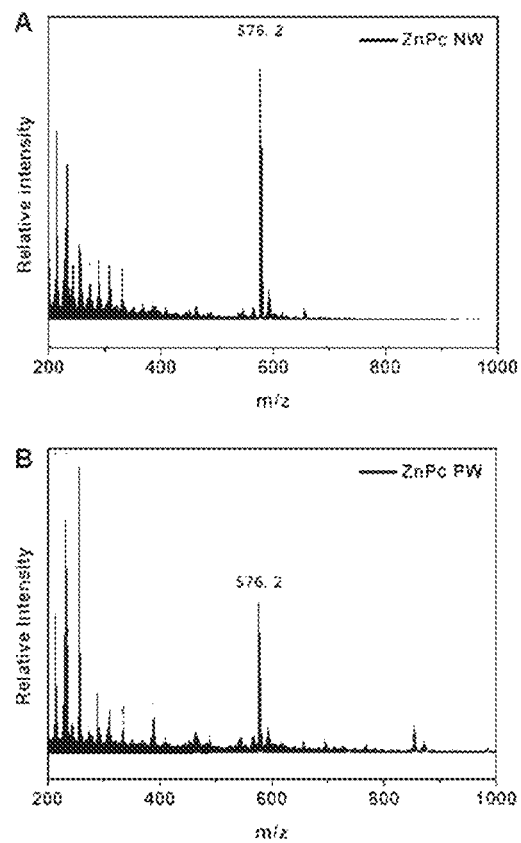

FIG. 6 shows the mass-spectra of α-form ZnPc nanowires (part A) and ZnPc powder (part B).

Figure 7:
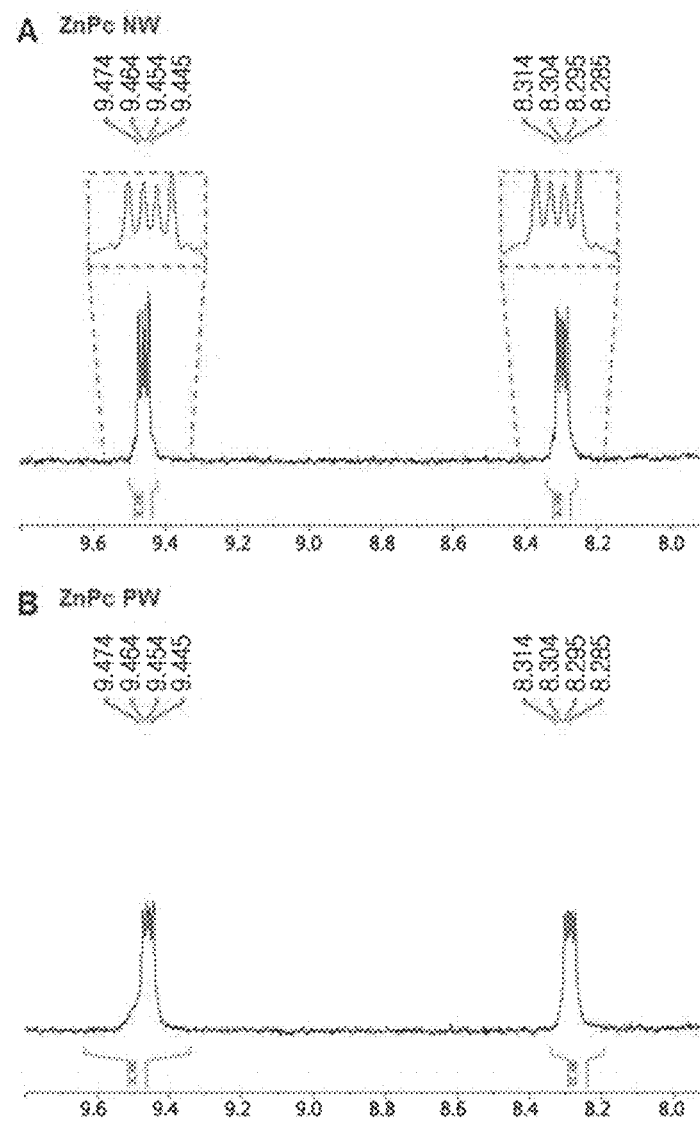

FIG. 7 shows the $^1$H NMR spectra of α-form ZnPc nanowires (part A) and ZnPc powder (part 7B).

Figure 8:
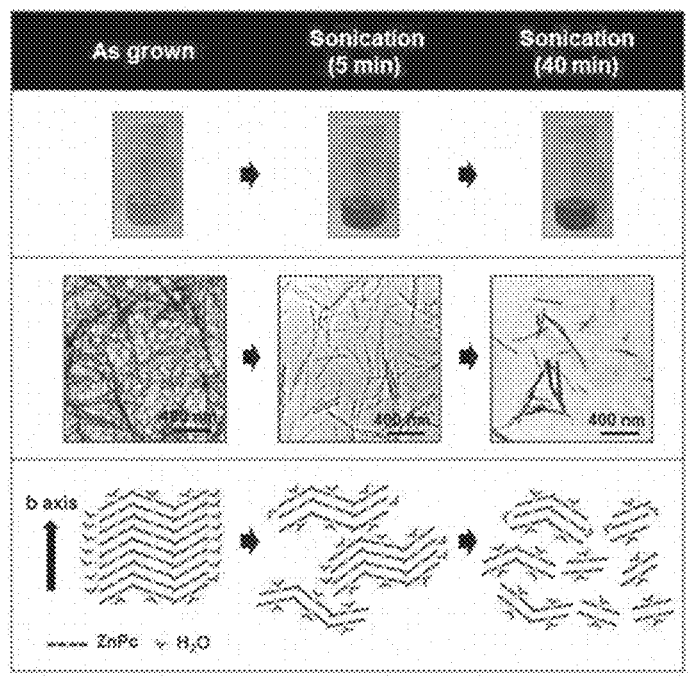

FIG. 8 shows the solubility of α-form ZnPc nanowires in water and the effect of sonication, in which the top row shows images of α-form ZnPc nanowire aqueous solutions, the middle row shows TEM images of α-form ZnPc nanowires, and the bottom row schematically shows the increased change of an interaction between water and ZnPc unit with longer sonication time, where the blue dashed lines indicate the hydrogen bonding between hydrogen atoms of water and nitrogen atoms of ZnPc.

Figure 9:
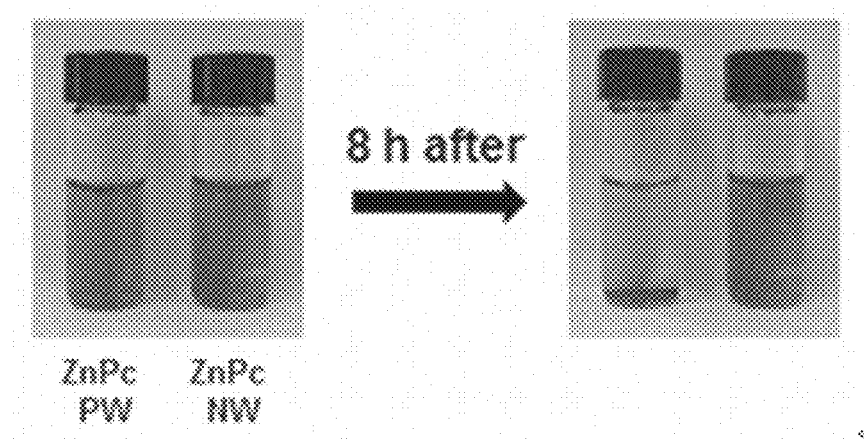

FIG. 9 shows the stability of ZnPc powder and α-form ZnPc nanowires in water.

Figure 10:
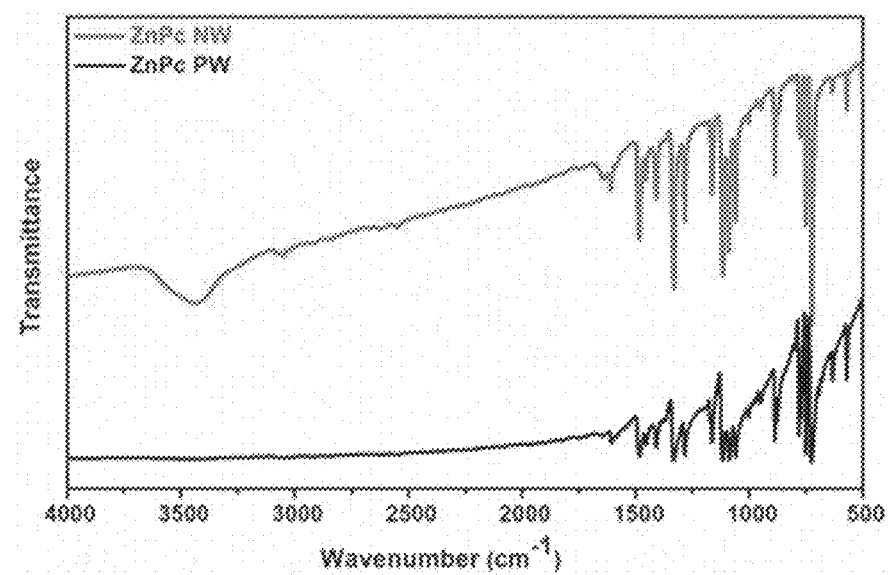

FIG. 10 shows the FT-IR spectra of α-form ZnPc nanowires (red line) and β-form ZnPc powder (black line), in which the α-form ZnPc nanowire bands show the O—H stretching vibration of water molecule at 3600 to 3300 cm$^{-1}$.

Figure 11:
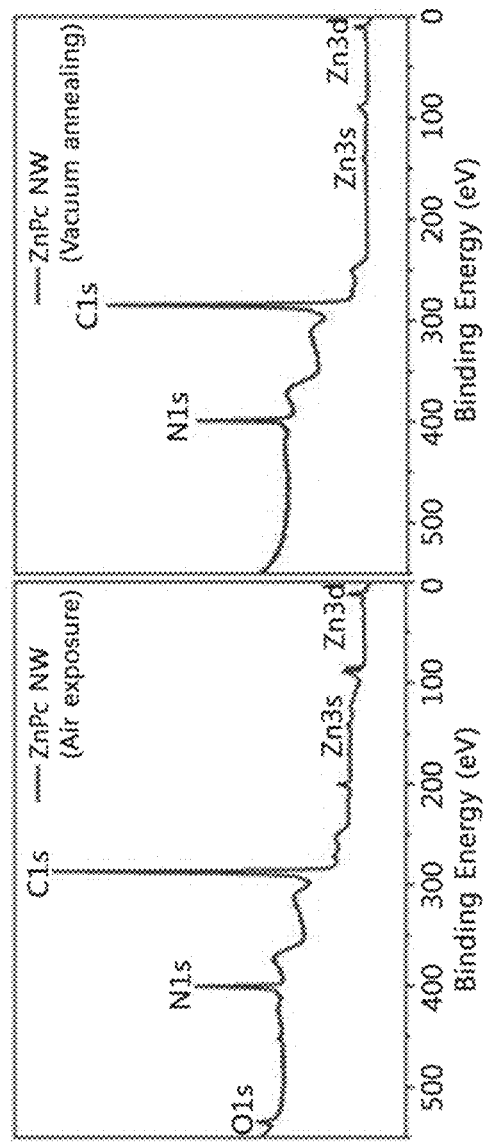

FIG. 11 shows the XPS survey spectra of α-form ZnPc nanowires exposed to air (left) and α-form ZnPc nanowires vacuum annealed (right), in which the O1s peak is observed at 533 eV due to adsorbed $H_2O$.

Figure 12:
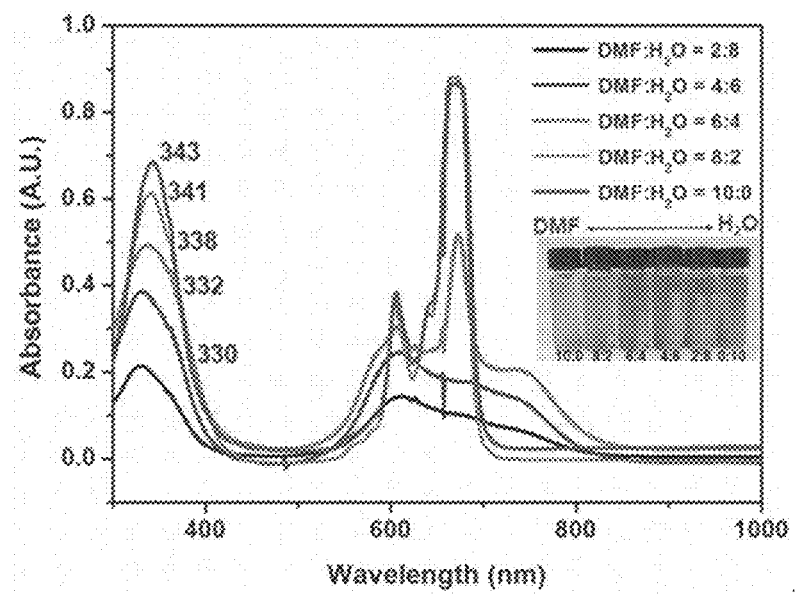

FIG. 12 shows the UV-vis absorption spectra of α-form ZnPc nanowires dissolved in a mixed solvent containing DMF and water in different ratios, in which with the increase of water content, the solution color changes to blue from 343 nm to 330 nm, and the insert shows an image of α-form ZnPc nanowire solution depending on the DMF/water ratio.

Figure 13:
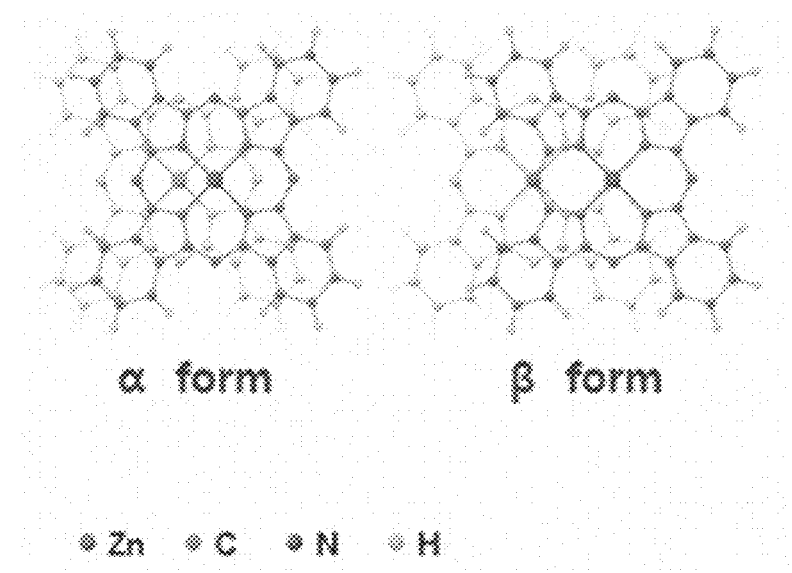

FIG. 13 shows the polymorphic structures of α-form and β-form ZnPc molecules.

Figure 14A:
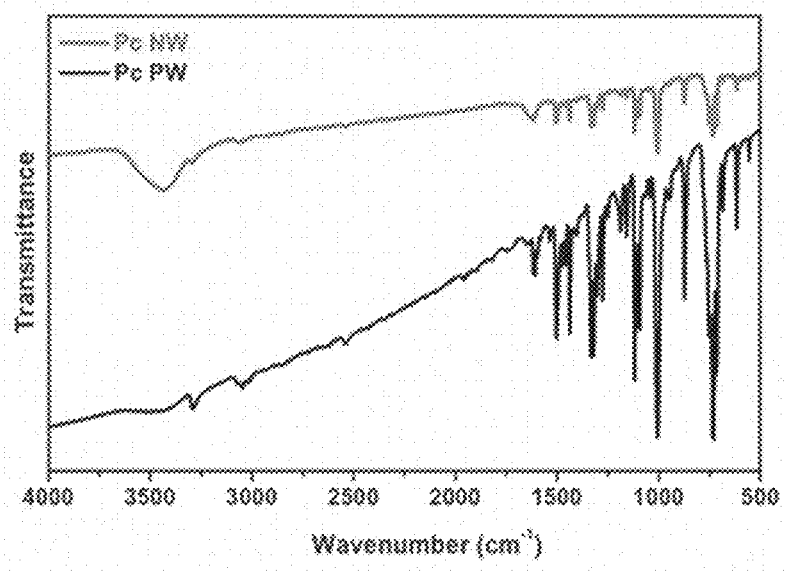

FIG. 14A shows the FT-IR spectra of Pc nanowire (red line) and Pc powder (black line), in which the O—H stretching bands at 3600 to 3300 cm$^{-1}$ are observed in the Pc nanowires, but not observed in the Pc powder, representing that the behaviors of α-form ZnPc nanowires and ZnPc powder are similar.

Figure 14B:
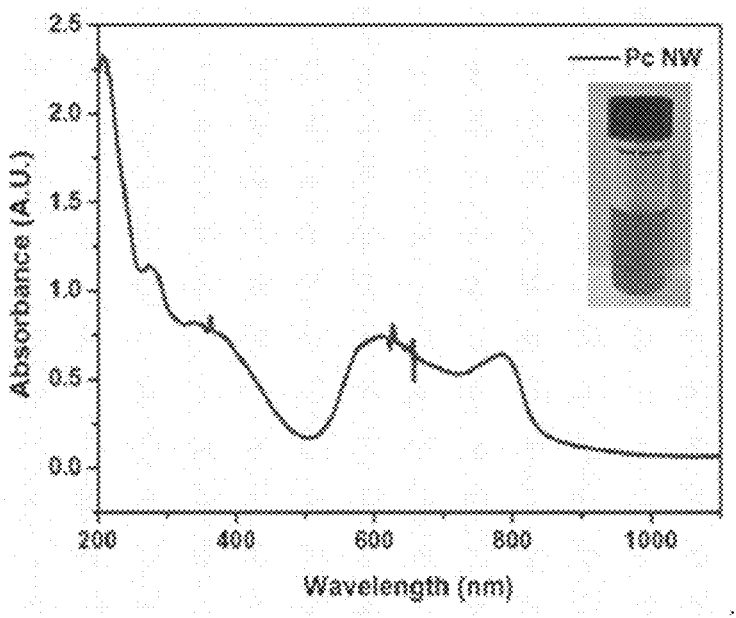

FIG. 14B shows the UV-vis spectrum of Pc nanowire solution, which shows well-resolved Soret and Q bands similar to those of α-form ZnPc nanowire aqueous solution, in which the insert shows an image of Pc nanowire aqueous solution.

Figure 15:
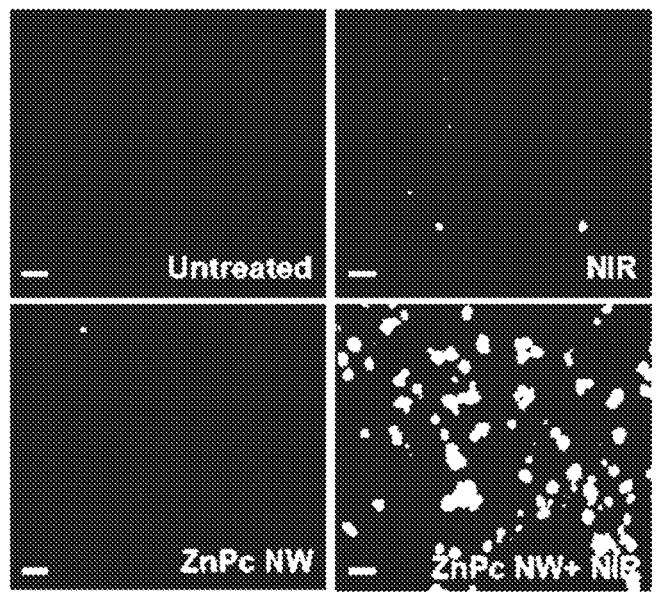

FIG. 15 shows fluorescence microscopy images of oral squamous cell carcinoma (KB cells) to detect oxidative stress using Image-iT™ LIVE Reactive Oxygen Species (ROS) Kit, in which the top left shows KB cells untreated, the top right shows KB cells irradiated with NIR (808 nm, 3 W/cm$^2$), the bottom left shows KB cells treated with α-form ZnPc nanowire solution (120 mg/L), the bottom right shows KB cells treated with α-form ZnPc nanowire solution (120 mg/L) followed by irradiation with NIR (808 nm, 3 W/cm$^2$), and the cells showing green fluorescence color represent oxidatively stressed cells affected with ROS.

Figure 16:
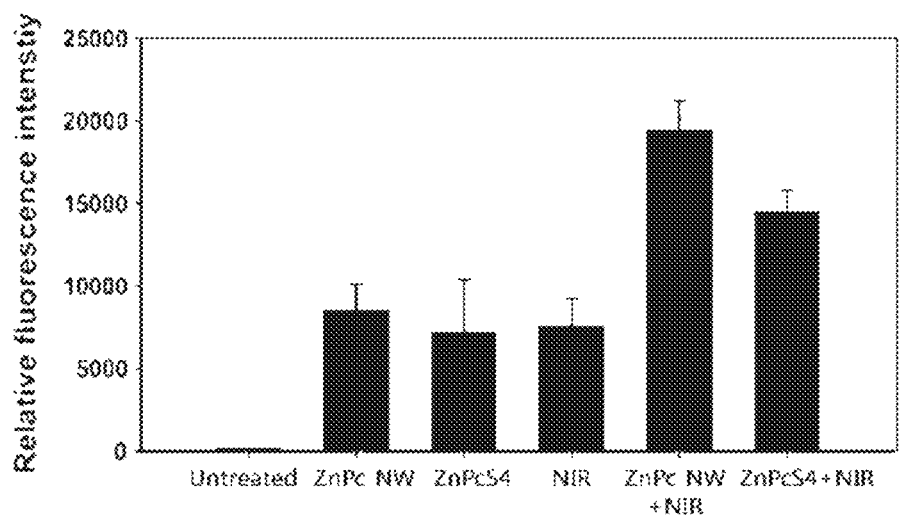

FIG. 16 shows the relative fluorescence intensity of each group, in which data are expressed as mean±standard deviation (n=3, triplicate).

Figure 17:
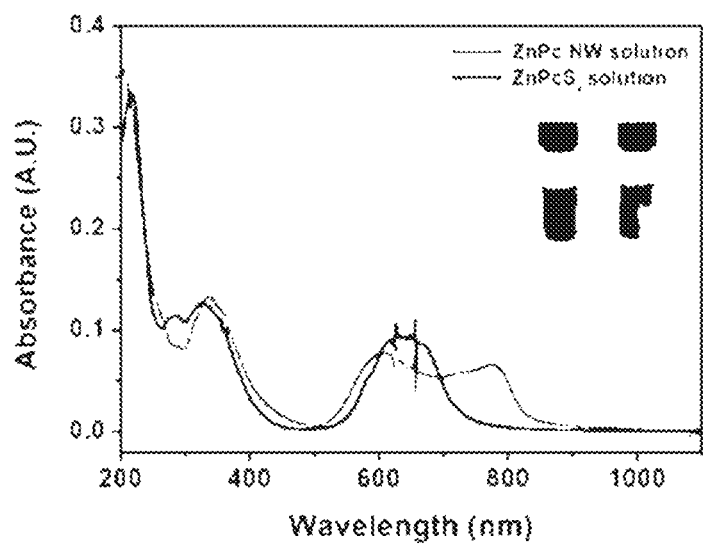

FIG. 17 shows the UV-vis spectra of α-form ZnPc nanowire solution (red line) and $ZnPcS_4$ solution (blue line), in which high absorptions of α-form ZnPc nanowire solution (at 600, 800 nm) and $ZnPcS_4$ solution (at 630 nm) in the NIR region are observed, and the inset shows an image of α-form ZnPc nanowire solution (blue, left) and $ZnPcS_4$ solution (aqua green, right).

Figure 18:
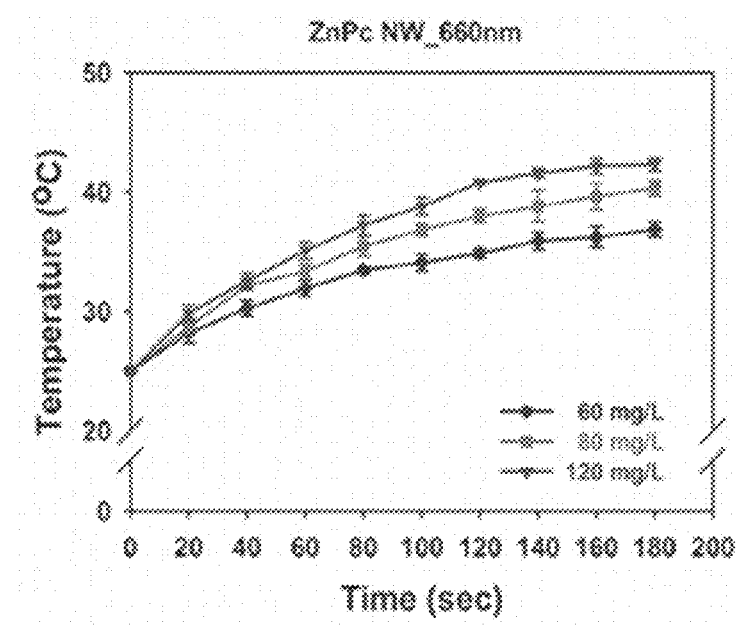
Figure 19:
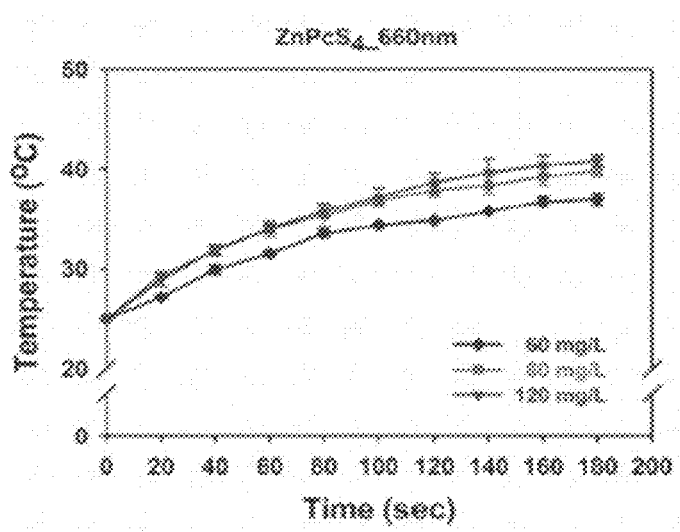

FIGS. 18 and 19 show the temperature changes of α-form ZnPc nanowire aqueous solution and $ZnPcS_4$ aqueous solution at various concentrations, respectively, upon NIR irradiation (660 nm, 3 W/cm$^2$) for 3 minutes.

Figure 20:
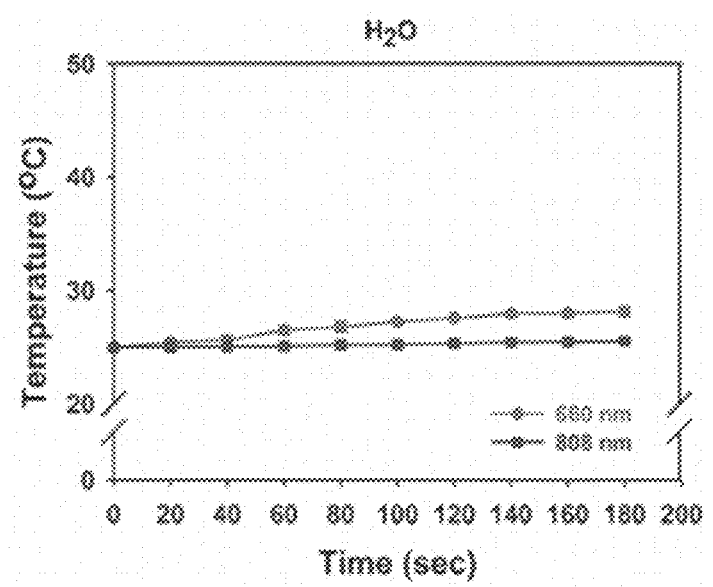

FIG. 20 shows the temperature changes of pure water upon NIR irradiation (660 nm and 808 nm, 3 W/cm$^2$) for 3 minutes.

Figure 21:
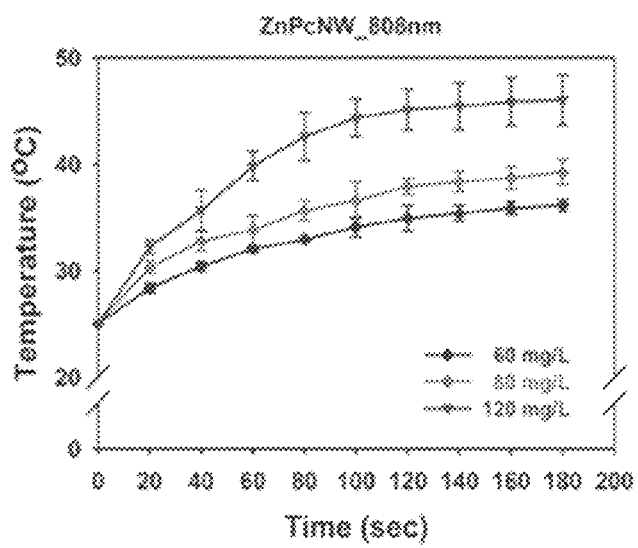
Figure 22:
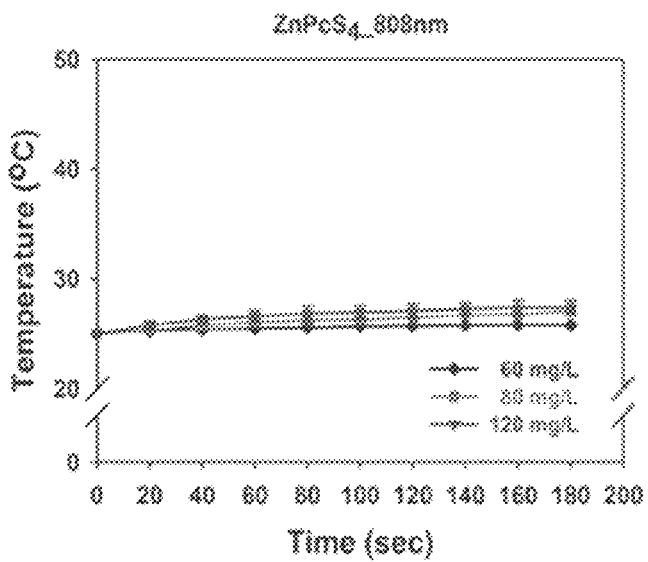

FIGS. 21 and 22 show the temperature changes of ZnPc nanowire aqueous solution and $ZnPcS_4$ aqueous solution at various concentrations, respectively, upon NIR irradiation (808 nm, 3 W/cm$^2$) for 3 minutes, in which data are shown as mean±SE (n=3, triplicate).

Figure 23:
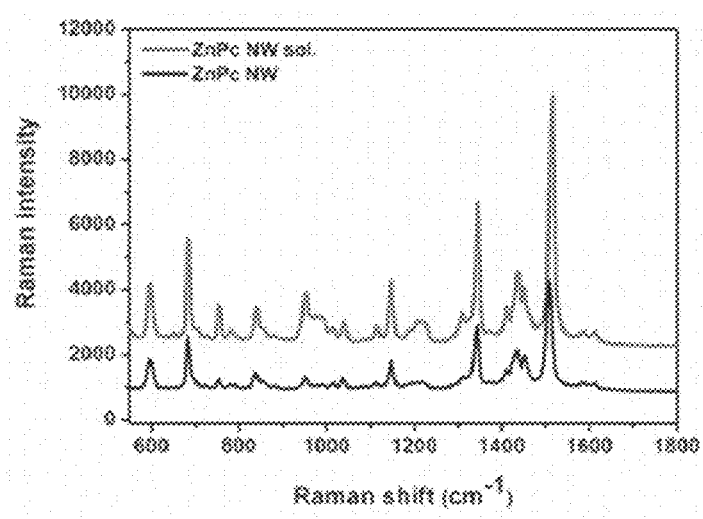

FIG. 23 shows the Raman spectra of α-form ZnPc nanowires grown on Si substrate (black line) and ZnPc nanowire aqueous solution (red line).

Figure 24:
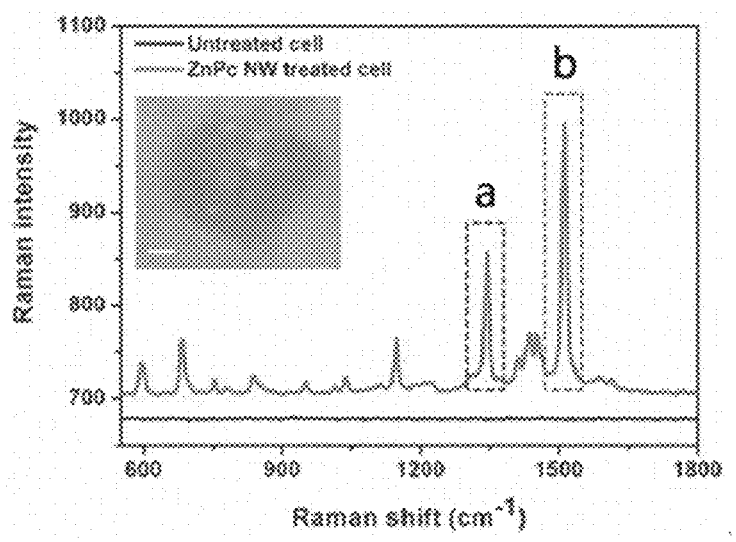

FIG. 24 shows the Raman spectra obtained from original KB cells (black line) and from KB cells treated with ZnPc nanowire solution (red line), in which the characteristic Raman peaks corresponding to the pyrrole stretching mode of ZnPc are observed at 1336 cm$^{-1}$ and 1506 cm$^{-1}$ and indicated by (a) and (b), and the insert shows an optical microscope image of a glass plate on which KB cells treated with α-form ZnPc nanowire solution are placed (scale bar: 4 μm).

Figure 25:
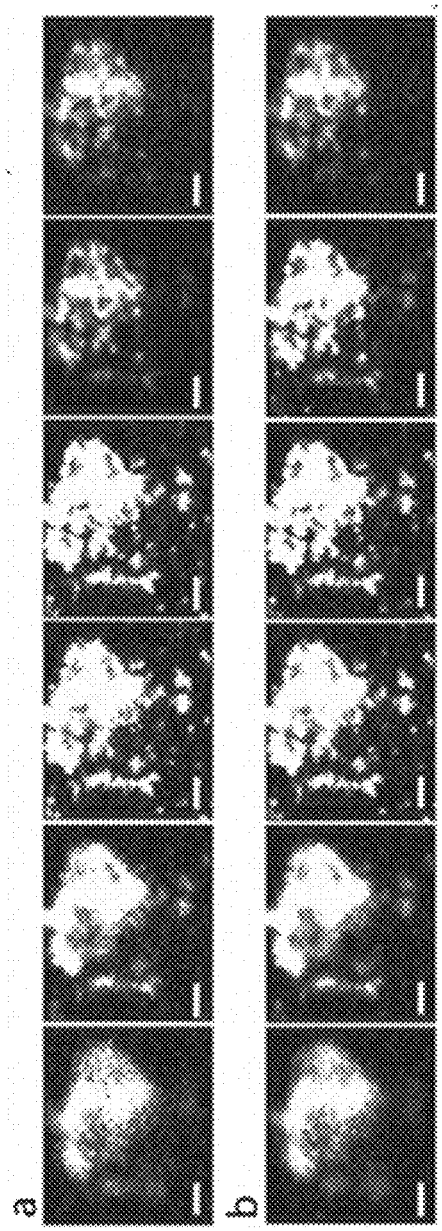

FIG. 25 shows confocal spectral images mapped with the peak intensities of (a) and (b) of FIG. 24, in which the vertical scan step (depth) is 2 μm, and the color brightness depends on the peak intensity (scale bar: 4 μm).

Figure 26:
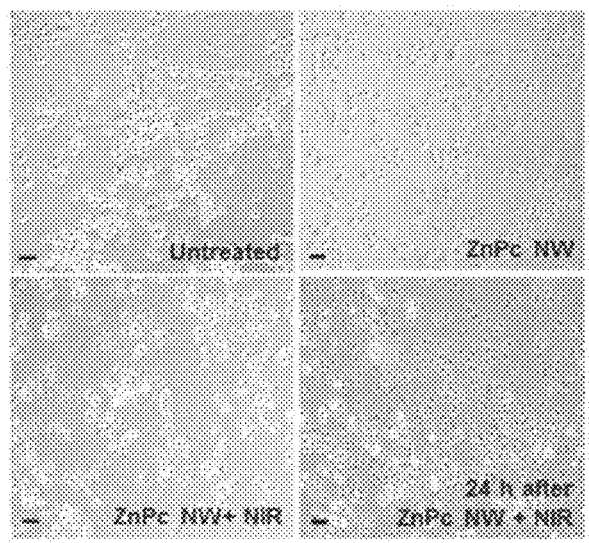

FIG. 26 shows bright-field microscopy images of KB cells, in which the top left shows KB cells untreated, the top right shows KB cells treated with α-form ZnPc nanowire solution (120 mg/L), the bottom left shows KB cells treated with ZnPc nanowire solution (120 mg/L) followed by irradiation with NIR (808 nm, 3 W/cm$^2$), and the bottom right shows KB cells 24 hours after phototreatment, in which the cells are stained with trypan blue, and the dead cells are observed in blue (scale bar: 4 μm).

Figure 27:
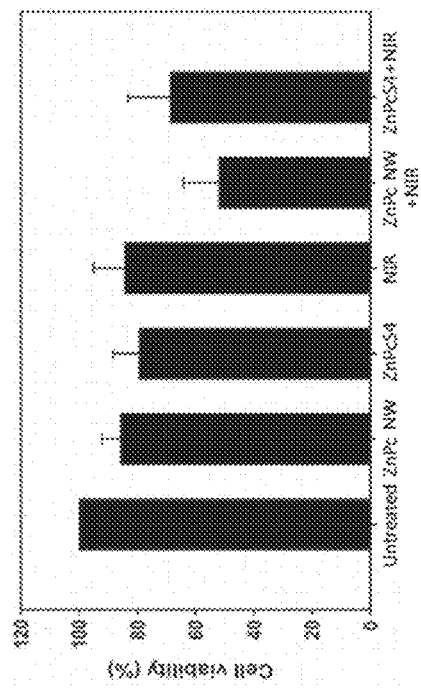

FIG. 27 shows the quantified KB cell viability from various experimental groups, in which data are expressed as mean±standard deviation (n=3, triplicate).

Figure 28:
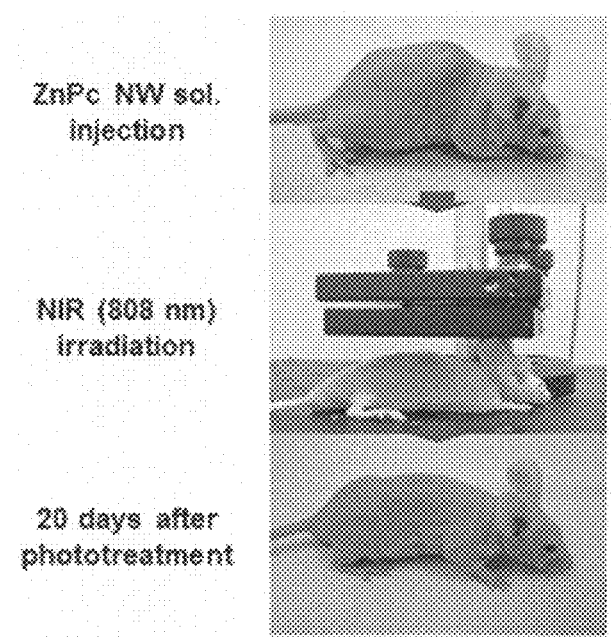

FIG. 28 shows images of in vivo phototherapy experiments, in which the top shows a mouse xenografted with KB tumor cells (tumor size: ca. 70 mm$^3$), the middle shows a mouse irradiated with NIR (808 nm, 3 W/cm$^2$) onto the tumor region where ZnPc nanowire solution (120 mg/L, 200 µl) is intratumorally injected, and the bottom shows a mouse twenty days after phototreatment (this mouse is healthy and not showing any abnormal behaviors).

Figure 29:
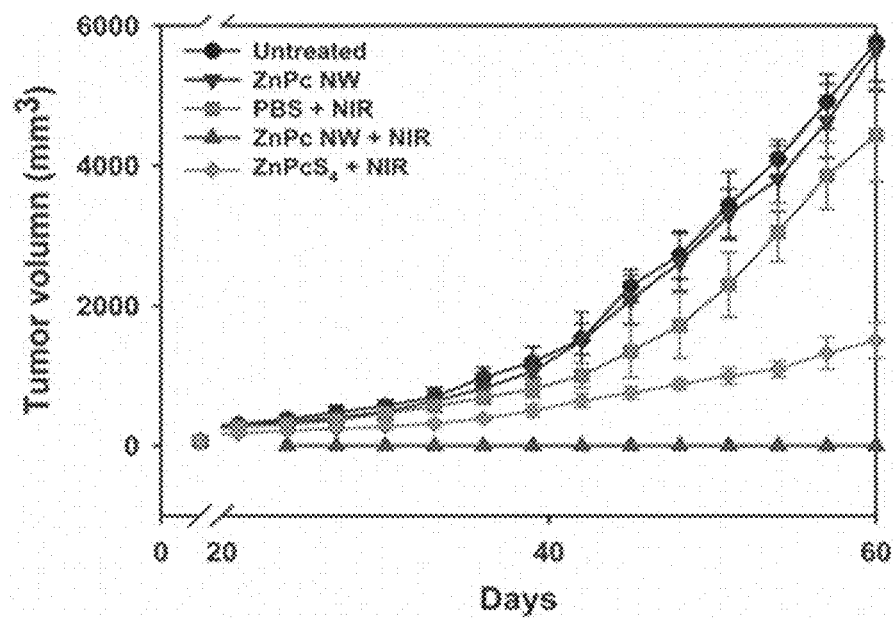

FIG. 29 shows the average tumor volume over time, in which the tumor volume is recorded three times a week, and data are expressed as mean±standard deviation (n=4, quadruplicate). Only the group treated with both ZnPc nanowire and NIR shows significant inhibition of tumor growth compared with untreated, α-form ZnPc nanowire, and PBS+NIR group (n=4, $P<0.05$, two-way ANOVA).

Figure 30:
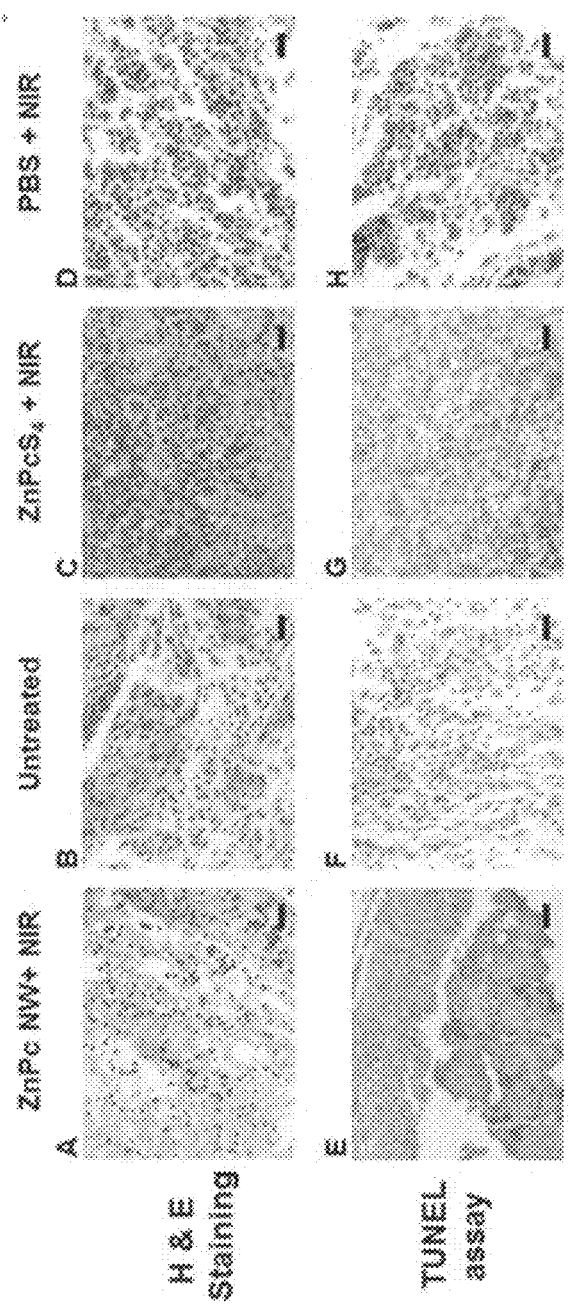

FIG. 30 shows representative histological images of tumor tissues treated with α-form ZnPc nanowires and irradiated with NIR, in which parts A to D show tumor tissues stained with H&E, where the darker pink stained cells represent dead cells, and parts E to H show the results of Deoxynucleotidyl transferase biotin-dUTP nick-end labeling (TUNEL) assay to detect specific apoptotic cells, where apoptotic cells are stained blue, and non-apoptotic cells are stained with hematoxylin (scale bar: 50 µm).

Figure 31:
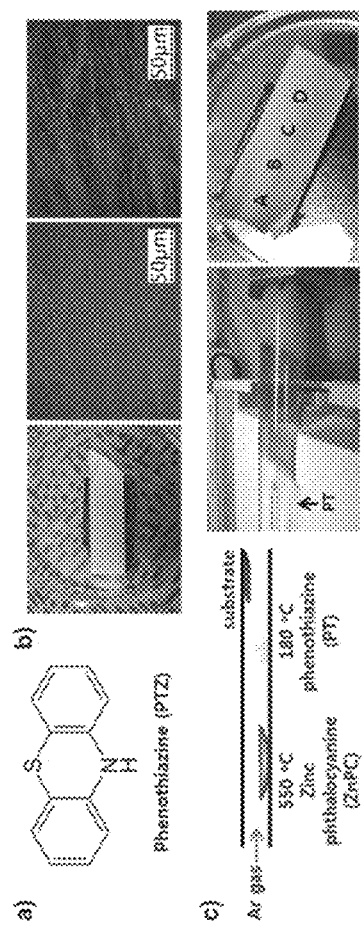

FIG. 31 shows a composite of α-form zinc-phthalocyanine nanowire/phenothiazine, in which part (a) shows the molecular structure of phenothiazine, part (b) shows an image of phenothiazine nanowire prepared on Si substrate by the VCR process, and an optical microscope image and a fluorescence microscopy image of nanowire structure, and part (c) shows the outline of the VCR process and an image of a zinc-phthalocyanine/phenothiazine composite prepared on Si substrate.

Figure 32:
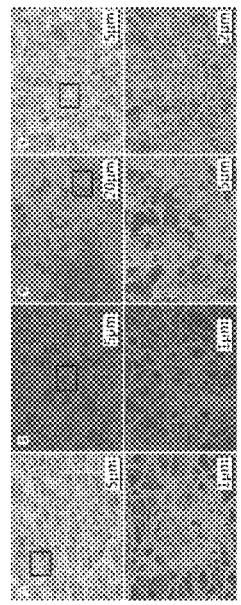

FIG. 32 shows SEM images of composites of α-form zinc-phthalocyanine nanowire/phenothiazine prepared differently depending on the position of Si substrate.

Figure 33:
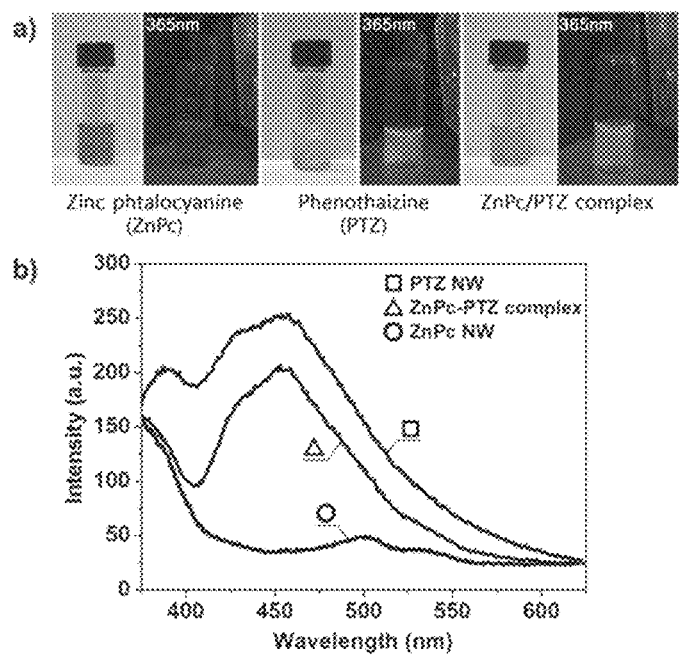

Part (a) of FIG. 33 shows fluorescence images of phenothiazine nanowire solution, α-form zinc-phthalocyanine nanowire solution, and composite solution of α-form zinc-phtalocyanine nanowire/phenothiazine when exposed to light at a wavelength of 365 nm, and part (b) of FIG. 33 shows fluorescence spectra of phenothiazine nanowire solution, α-form zinc-phthalocyanine nanowire solution, and composite solution of α-form zinc-phtalocyanine nanowire/phenothiazine at a wavelength of 340 nm.

MODE FOR INVENTION

In the following, the present invention will be described in more detail with reference to Examples, Comparative Examples, and Experimental Examples. However, the following Examples, Comparative Examples, and Experimental Examples are provided for illustrative purposes only to facilitate understanding of the present invention, and the scope of the present invention is not limited thereto.

Example 1

Preparation of α-Form Zinc-Phthalocyanine Nanowires

Through a solid-vapor transport reaction, called the vaporization-condensation-recrystallization (VCR) process, using ZnPc powder as a precursor, α-form zinc-phthalocyanine nanowires were prepared.

Specifically, ZnPc powder (0.05 g, Sigma-Aldrich) was loaded in a ceramic boat, which was located at the center of a quartz tube placed in an electrical heating furnace system. Before the reaction, the quartz tube was flushed with Ar gas at a flow rate of 800 sccm for 5 minutes to remove trapped ambient gases and then heated up to 550° C. under steady Ar flow. A Si(100) substrate (wafer, WRS materials) was placed at the end region (downstream) of the furnace.

Figure 1A:
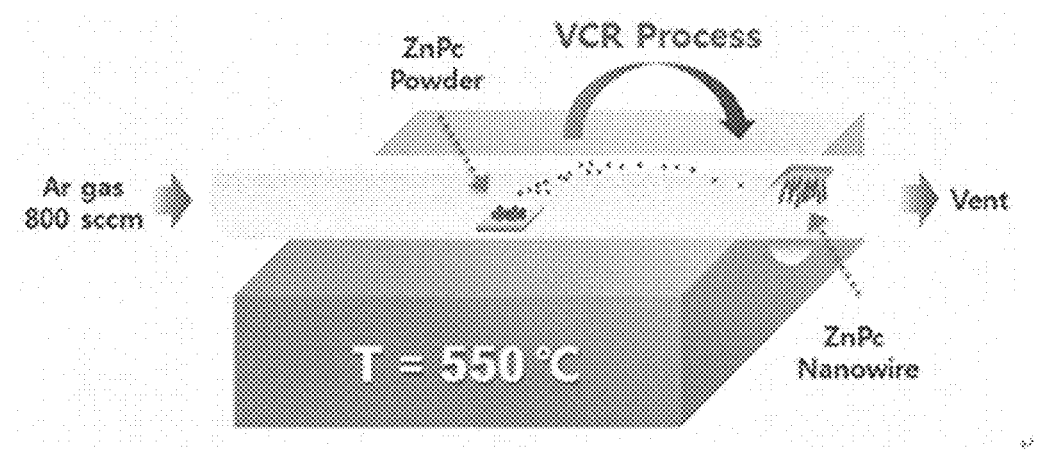
FIG. 1A schematically shows the VCR process growing α-form ZnPc nanowires of the present invention.

During the reaction, the ZnPc powder placed at the center of a tube-type hating furnace was vaporized at 550° C., and ZnPc vapors were delivered by Ar gas downstream where the Si wafer was located. The ZnPc vapors were condensed on the Si wafer as the substrate temperature was naturally lowered to 180° C., at which one-dimensional ZnPc nanowires grow. The reaction was maintained for 40 minutes for the growth of ZnPc nanowires and then the sample was cooled to room temperature under Ar flow. This VCR process is schematically shown in FIG. 1A.

Experimental Example 1

Characterization of α-Form Zinc-Phthalocyanine Nanowires

The following experiment was performed to determine the morphology, chemical elements, and diffraction patterns of α-form zinc-phthalocyanine nanowires prepared in Example 1.

1. SEM Measurement

Au was sputtered on α-form zinc-phthalocyanine nanowires prepared in Example 1 for scanning electron microscopy (SEM, JSM-7410F, JEOL) measurement. The obtained SEM image is shown in FIG. 1B.

Figure 1B:
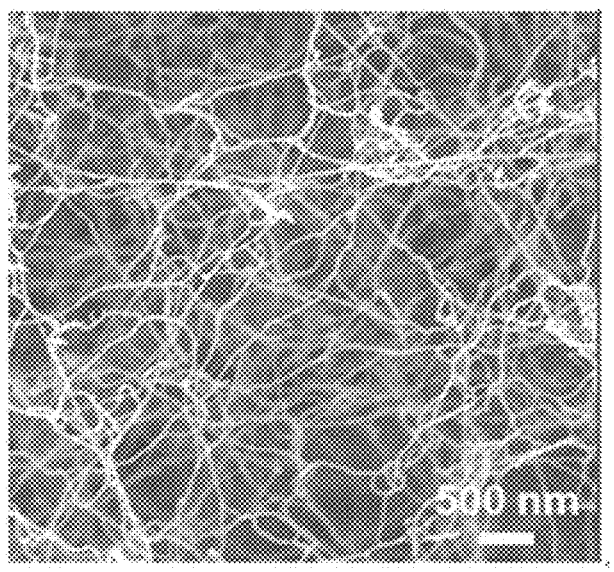
FIG. 1B shows an SEM image of α-form ZnPc nanowires obtained by the VCR process.

As shown in FIG. 1B, it was found that the diameter and length of α-form zinc-phthalocyanine nanowires were about 50 to 100 nm and about 1 to 10 µm, respectively.

2. XRD Measurement

The crystal structure of α-form zinc-phthalocyanine nanowires prepared in Example 1 was characterized by X-ray powder diffraction (XRD, D/MAX-2500/PC, RIGAKU)) and high-resolution transmission electron microscopy (HR-TEM, JEM 2100F, JEOL)) with selected area electron diffraction (SAED) data.

Figure 1C:
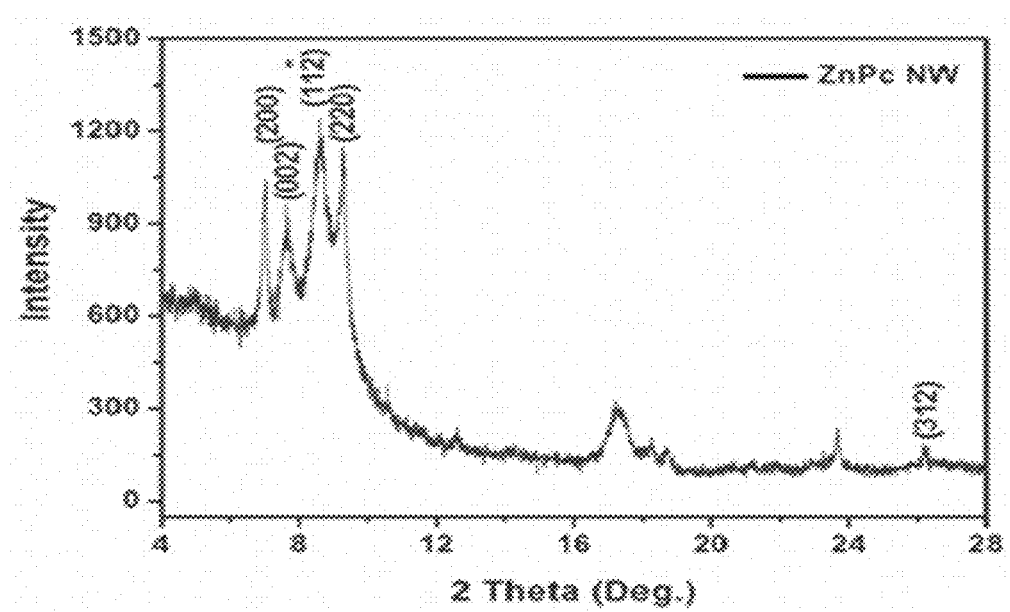
FIGS. 1C and 1D show XRD patterns of ZnPc nanowires (α-form) and ZnPc powder (β-form) collected from Si(100) substrate, respectively.
Figure 1D:
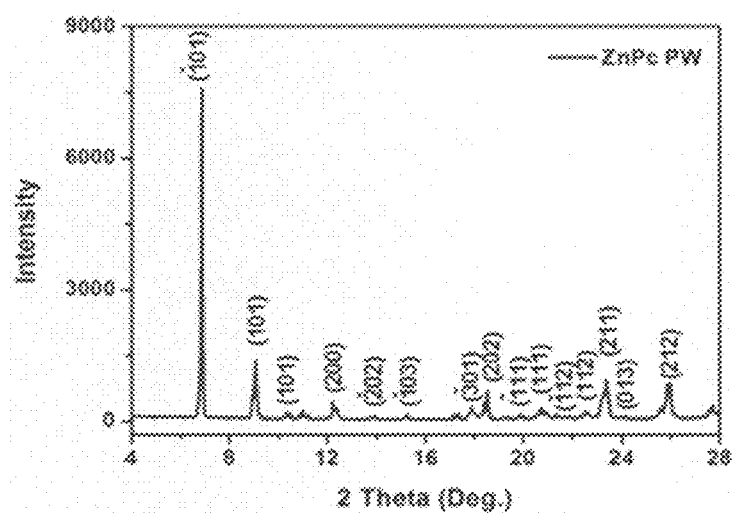

XRD patterns of ZnPc nanowires (α-form) and ZnPc powder (β-form) collected from Si(100) substrate, respectively, are shown in FIGS. 1C and 1D.

As shown in FIGS. 1C and 1D, according to the JC-PDS cards No. 21-1986 and 39-1882, the XRD results reveal that ZnPc nanowire has an α-form, whereas the original ZnPc powder has a β-form. One of the characteristic XRD peaks of ZnPc is the (200) peak. While the β-form ZnPc nanowire shows $d_{(200)}$=7.24 Å (at 2θ=12.22°), the α-ZnPc nanowire shows $d_{(200)}$=12.6 Å (at 2θ=7.01°), which agrees well with previously reported values from α-form ZnPc crystal and thin film.

3. FT-IR Measurement

The α-form ZnPc nanowires and β-form ZnPc powder were characterized using Fourier-transformed infrared (FT-IR) spectroscopy. Specifically, for the FT-IR spectroscopy, KBr pellets of ZnPc powder and ZnPc nanowires were prepared, and the FT-IR spectra were obtained using an FT-IR spectrophotometer (VERTEX 70, Bruker Optics). The results are shown in FIG. 2.

Figure 2:
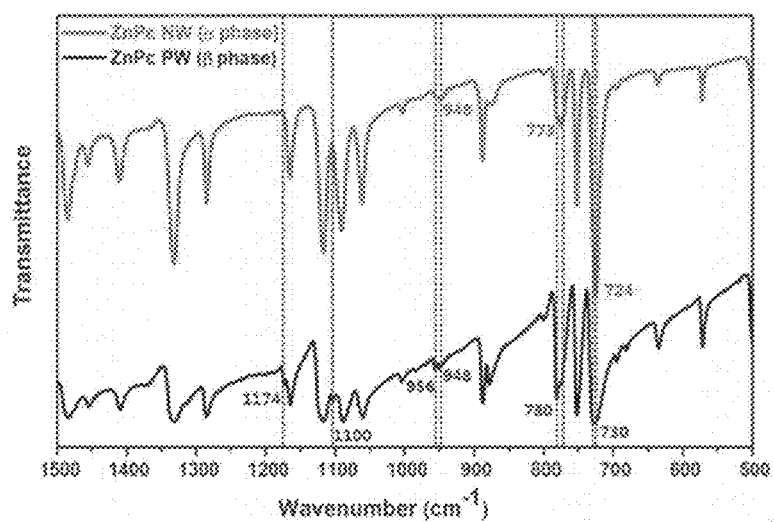
FIG. 2 shows the FT-IR spectra of α-form ZnPc nanowires (red line) and β-form ZnPc powder (black line).

As shown in FIG. 2, the FT-IR spectroscopy results further confirm the genuineness of the α-form of ZnPc nanowire (red line) as it displays a fingerprint-bending mode of C—H at 724 $cm^{-1}$ together with the vibrational mode of the center cyclic ring at 773 $cm^{-1}$. Large quantities of α-form ZnPc nanowires can be collected from multiple reaction batches for the powder XRD measurements.

4. Thermogravimetric Analysis

Thermogravimetric measurement of α-form ZnPc nanowires was carried out using a thermogravimetry analyzer (TG- 2171, Cahn Instrument Inc.). 5 mg of ZnPc powder (Sigma-Aldrich) was loaded and heated from room temperature to 1000° C. at a rate of 4° C./min under Ar atmosphere. The obtained results are shown in FIG. 3.

Figure 3:
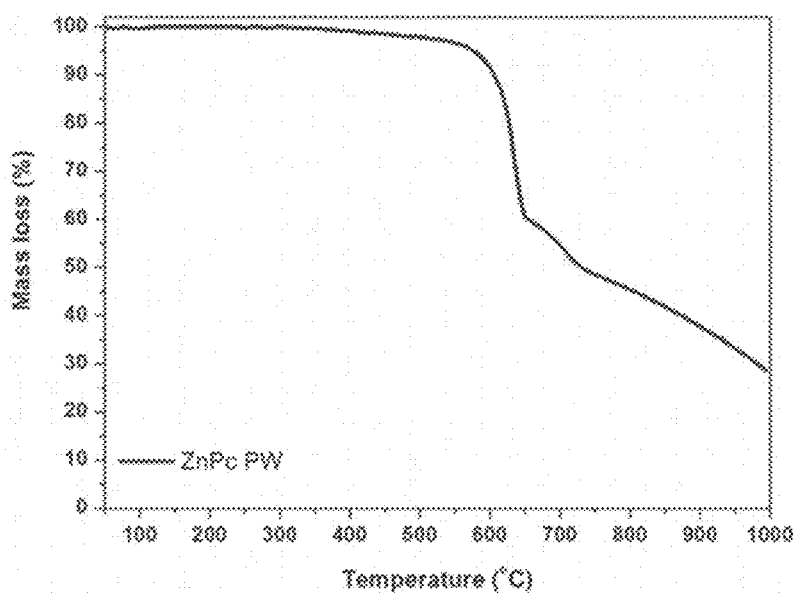
FIG. 3 shows the results of thermogravimetric analysis (TGA) of α-form ZnPc nanowires.

As shown in FIG. 3, it can be seen that the thermal vaporization of ZnPc starts at 550° C.

5. HR-TEM Measurement

HR-TEM measurement was performed using samples prepared by dropping an aqueous solution of α-form ZnPc nanowires onto a carbon film-coated Cu grid (TED PELLIA Inc. USA). The results of HR-TEM measurement are shown in FIG. 4.

As shown in FIG. 4, the HR-TEM image shows that the α-form ZnPc nanowire has well-defined crystalline lattices parallel to the growth direction. The single crystallinity is confirmed from a SAED pattern that exhibits individual diffraction spots (the insert in part A). The (002) lattice spacing of 1.14 nm (part B) agrees well with the XRD result ($d_{(002)}=$ 11.5 Å at 2θ=7.66°). The individual lattice lines ((200) planes along the [100] direction) correspond to linear Zn metal ion arrays as depicted by the red lines (in part C). The growth of α-form ZnPc nanowire follows the direction of self-assembly of ZnPc molecules via π-π stacking, so the (200) planes are parallel to the growth direction.

6. XRD Measurement of α-Form ZnPc Nanowires Grown on Si Substrate

XRD patterns of α-form ZnPc nanowires grown on a Si(100) substrate were measured using an X-ray diffractometer (XRD, D/MAX-2500/PC, RIGAKU), and the results are shown in FIG. 5.

As shown in FIG. 5, indeed, when as-grown α-form ZnPc nanowires on the Si substrate are examined, only a single XRD peak from the (200) planes appears because most of the α-form ZnPc nanowires prefer to lay down on the substrate with the (200) planes parallel to the substrate. The structure of α-form ZnPc nanowire of the present invention is closely comparable to the previously reported CuPc nanowire.

7. Mass Spectrum and NMR Spectrum Measurements

The preservation of molecular structure of ZnPc in α-form ZnPc nanowire without any skeletal destruction during the VCR process was confirmed by mass spectroscopy and nuclear magnetic resonance (NMR) spectroscopy. Specifically, the integrity of α-form ZnPc nanowires was characterized by fast atom bombardment-mass spectrometry (FAB-MS, IMS 700 high-resolution mass spectrometer equipped with FAB ionization, JEOL) and $^1$H nuclear magnetic resonance (NMR, DMSO-$d_6$, FT-300 MHz Bruker Aspect 3000).

The results of mass spectra and NMR spectra of α-form ZnPc nanowires (part A) and ZnPc powder (part B) are shown in FIGS. 6 and 7.

As shown in FIG. 6, the mass spectra display basically identical chemical compositions for both α-form ZnPc nanowire and powder as the intense peak at 576.2 m/z, corresponding to the exact mass of ZnPc (576.079 m/z), appears from both samples.

Moreover, as shown in FIG. 7, the proton ($^1$H) NMR spectrum of the α-form ZnPc nanowire further proves that the α-form ZnPc nanowire contains pure ZnPc without any structural change.

The results of mass spectrum and NMR spectrum are as follows:

MS (m/z calculated, 576.079 [M$^+$]. found, 576.2 [M$^+$]), $^1$H NMR [ZnPc powder: δ 9.445-9.473 (dd, $J_1$=5.6, $J_2$=3, 8H ArH); δ 8.274-8.302 (dd, $J_1$=5.6, $J_2$=3, 8H ArH);

ZnPc 나노와이어: δ 9.445-9.474 (dd, $J_1$=5.7, $J_2$=3, 8H ArH); δ 8.285-8.314 (dd, $J_1$=5.7, $J_2$=3, 8H ArH)].

Experimental Example 2

Investigation of Water-Solubility of α-Form ZnPc Nanowires

1. TEM Images and Stability of α-Form ZnPc Nanowire Aqueous Solution

An α-form ZnPc nanowire solution was prepared by adding 1 mg of α-form ZnPc nanowires collected from Si substrates into 5 ml of water, followed by sonication for various times in a bath sonicator (UC-10, JEIOTECH). The final solution was transferred for the measurement of optical absorbance using a UV-vis spectrometer (Agilent 8453 spectrophotometer). The concentration of the α-form ZnPc nanowire solution was determined by measurement of optical absorbance at 219 nm. The calibration curve was made by measuring the optical absorbance of a sequentially diluted solution at 219 nm.

The observation results and TEM images of the α-form ZnPc nanowire solution are shown in FIG. 8 and the results of stability are shown in FIG. 9.

As shown in the top row of FIG. 8, it was found that the α-form ZnPc nanowires were well dissolved in water with short mechanical agitation by sonication. On the contrary, it was found that the water solubility did not increase in the ZnPc powder even with similar treatment.

Moreover, as shown in the middle row of FIG. 8, the degree of dispersion of α-form ZnPc nanowires in water gradually increases as a function of sonication time, which is easily noticed by the color change of the solution from transparent pale blue to dark blue, which shows the increased change of an interaction between water and α-form ZnPc unit.

Furthermore, as shown in FIG. 9, it was found that the α-form ZnPc nanowire aqueous solution is highly stable at room temperature as it stays for over three months without any aggregation, but the ZnPc nanowire sonicated in water precipitates in a short period of time.

2. FT-IR and XPS measurements of α-form ZnPc nanowires

The dispersion of α-form ZnPc nanowires in water should involve the preferred adsorption of water molecules to α-form ZnPc nanowires. The preferred interaction of water on α-form ZnPc nanowires over ZnPc powder was confirmed by Fourier transformed infrared (FTIR) spectroscopy (VERTEX 70, Bruker Optics) and X-ray photoelectron spectroscopy (XPS, manufactured by the Pohang Accelerator Laboratory). X-ray photoelectron spectra (XPS) were acquired from the 8A1 beamline of the synchrotron facility at Pohang Accelerator Laboratory, POSTECH. The photon energy was 630 eV. The obtained results are shown in FIG. 10 (FR-IR spectra) and FIG. 11 (XPS).

As shown in FIG. 10, upon exposure of both samples (nanowire/powder) in air (humidity: 30%) for 2 hours, ZnPc nanowire showed the O—H vibrational band from the water molecule at 3600 to 3300 cm$^{-1}$, which was absent for ZnPc powder PW.

Moreover, the XPS data of FIG. 11 confirm the preferred adsorption of water molecules to α-form ZnPc nanowire (the XPS spectra of α-form ZnPc nanowire also exhibits the O1s peak at 533 eV corresponding to the 0 in water). The O1s peak disappears when the sample is vacuum annealed.

3. Measurement of Binding of α-Form ZnPc Nanowire to Water

The preferred adsorption of water to α-form ZnPc nanowire occurs through hydrogen bonding of water to the N atoms in ZnPc and coordination of water to the Zn(II) ion in ZnPc. Although the hydrogen bonding of water to N atoms in ZnPc is easily agreed, the coordination of water to Zn(II) ions still needs to be confirmed. Therefore, the coordination power of water molecules to the central Zn(II) ion was examined by adding water into a DMF solution of ZnPc nanowire at various volume ratios.

Specifically, 0.5 mg of α-form ZnPc nanowires was dissolved in dimethylformamide (DMF), and water was added to make a mixture solution at various ratios (DMF:$H_2O$=2:8, 4:6, 6:4, 8:2, 10:0). The mixture solution was examined for the shift of the Soret band using a UV-vis spectroscopy (Agilent 8453 spectrophotometer).

The UV-vis absorption spectra of α-form ZnPc nanowires dissolved in a mixed solvent containing DMF and water in different ratios are shown in FIG. 12.

As shown in FIG. 12, the UV-vis spectrum of pure α-form ZnPc nanowire/DMF solution shows characteristic Soret and Q bands at 343 nm and 669 nm, respectively. Upon increase of water fraction, the Soret band gradually shifts to higher energy (up to 330 nm), and the solution color changes from green to blue. The blue shift of the Soret band implies that DMF molecules pre-coordinated to the Zn(II) ion are replaced by water molecules that have stronger coordination power.

While both the hydrogen bonding and coordination of water to Zn(II) ion interactions are equally applicable to both ZnPc powder and α-form ZnPc nanowires, the main factor associated with the substantial increase in the solubility of ZnPc nanowires in water highly depends on both the hydrogen bonding of water to the N atoms of ZnPc and the coordination of water to the Zn(II) ion in ZnPc in the case of α-form ZnPc nanowires.

4. Measurement of Structure of α-Form ZnPc Nanowires

FIG. 13 shows the polymorphic structures of α-form and β-form ZnPc molecules. The site where both the hydrogen bonding and coordination of water to the Zn(ii) ion are available is wider in ZnPc nanowire (α-form) than in ZnPc powder. The reason for this is that all Zn(II) ions in β-form powder are pre-coordinated to the framework nitrogen atoms of neighboring ZnPc (FIG. 13), resulting in the loss of both Zn(II) and N interaction sites. This is the main reason for the high stability of β-form ZnPc powder. On the contrary, all of the hydrogen bonding and water coordination sites are freely available in α-form ZnPc nanowire. Among the α-form ZnPc nanowires, shorter α-form ZnPc nanowire has a large surface area, which exhibits higher water solubility (see FIG. 8).

5. FT-IR and UV-Vis Spectrum Measurements of Metal-Free α-Form Nanowires

Meanwhile, FIGS. 14A and 14B show the FT-IR spectra (VERTEX 70, Bruker Optics) and UV-vis spectra (Agilent 8453 spectrophotometer) of metal-free phthalocyanine (Pc) nanowire solution, from which it can be seen that the metal-free phthalocyanine nanowires also show significantly increased water solubility. Based on this, it is considered that the hydrogen bonding seems to have a more important role for the increase in water solubility of α-form ZnPc nanowires together with the water coordination to Zn(II).

Experimental Example 3

Measurement of Dual Photoeffect of ZnPc Nanowires

Metallo-phthalocyanine (MPc) generates either reactive oxygen species or thermal energy upon light illumination in the near infrared region depending on the electronic configuration of the central metal. When a central metal possesses $d^0$ or $d^{10}$ (closed shell, like Zn(II)) electronic configuration, the triplet excited state has a long lifetime sufficient to be involved in the generation of ROS (PD effect). On the other hand, MPc having central metals of which the d orbitals are not completely occupied (open shell, like Ni(II), Co(II), etc.) shows low PD effect, but rather exhibits fast conversion of excited electronic energy to the vibrational mode, resulting in a PT effect.

Because the required conditions of the electronic energy states of photosensitizers for PD and PT effects mutually conflict (i.e., the triplet excited state of the photosensitizer with long lifetime is advantageous to the PD effect but disadvantageous to the PT effect), it is difficult to realize photosensitizers that exhibit both photo effects simultaneously. To enable such a dual phototherapy, composites containing two components generating PD and PT effects have been suggested. Examples include a ZnPc-encapsulated carbon nanohorn and an indocyanine greenconjugated gold nanorod.

1. Measurement of PD Activity of α-Form ZnPc Nanowires

The α-form ZnPc nanowire itself shows both PD and PT effects upon NIR illumination. The PD activity of α-form ZnPc nanowire was proven by detecting reactive oxygen species generated upon illumination with NIR upon irradiation with NIR ($\lambda$=808 nm) laser. The reactive oxygen species generated from NIR-activated KB cells containing α-form ZnPc nanowires was assessed using Image-iT™ LIVE Reactive Oxygen Species (ROS) Kit.

This experiment is based on 5-(and-6)-carboxy-2'7'-dichlorodihydrofluorescein diacetate (carboxy-$H_2$DCFDA) as a fluorogenic marker for ROS permeated viable cells. In the presence of ROS, the reduced carboxy-$H_2$DCFDA is supposed to be oxidized to emit bright green fluorescence. Therefore, the oxidatively stressed cells by ROS could be recognized by green fluorescence.

To compare the effect of α-form ZnPc nanowire, commercially available ZnPcS$_4$ specially designed to increase water solubility was used in the experiment.

The generation of reactive oxygen species (ROS) was monitored using Image-iT™ LIVE Reactive Oxygen Species Kit based on $H_2$DCFDA (Molecular Probes/Invitrogen), following the manufacturer's protocol. Pre-seeded epidermoid mouth carcinoma cells (KB cells) were incubated with ZnPc nanowire solution (120 mg/L) at 37° C. with 5% $CO_2$ for 18 hours. Then, after washing the cells thoroughly with phosphate buffer saline (PBS), the cells were irradiated with an 808 nm laser. $H_2$DCFDA (10 μM) was added to the cells and, and the cells were incubated at 37° C. for 30 minutes. $H_2$DCFDA is a fluorogenic marker for ROS, which permeates live cells and is deacetylated by intracellular esterases. In the presence of ROS, the reduced fluorescein compound is oxidized and emits bright green fluorescence. Fluorescence intensity was measured at 529 nm using a fluorescence spectrometer (Cary Eclipse, Varian).

The results are shown in FIGS. 15 and 16.

As shown in FIGS. 15 and 16, the amounts of ROS generated by cells untreated, cells treated with α-form ZnPc nanowires, cells treated with ZnPcS$_4$ and irradiated with NIR were insignificant. However, the cells treated with α-form ZnPc nanowires and irradiated with NIR showed strong green fluorescence intensity. These results indicate that the α-form ZnPc nanowires excited by NIR are the main factor for the ROS generation.

2. Measurement of PT Property of α-Form ZnPc Nanowires

The PT property was examined by monitoring temperature changes of α-form ZnPc nanowire aqueous solutions (60, 80, 120 mg/L) upon light illumination at two different wavelengths (λ) of 660 nm, at which the highest absorption occurs, and 808 nm, at which most biological systems become transparent, at the power of 3 W/cm$^2$.

The α-form ZnPc nanowire solution and zinc phthalocyanine tetrasulfonate (ZnPcS$_4$) solutions at various concentrations (60, 80, 120 mg/L) were irradiated using a 660/808 nm laser (diode laser, JENOPTIK unique-mode GmbH, Germany) at 3 W/cm$^2$. The temperature of each solution was measured with a thermocouple connected temperature controller (Hanyoung, Korea) at 20-second intervals for a total of 3 minutes. Three sets per each solution were measured.

The UV-vis spectra of α-form ZnPc nanowire solution and ZnPcS$_4$ solution are shown in FIG. 17, and the temperature changes of α-form ZnPc nanowire aqueous solution, ZnPcS$_4$ aqueous solution, and water upon NIR irradiation (660 nm and 808 nm) are shown in FIGS. 18 to 22.

As shown in FIG. 17, the emergence of an unprecedented PT property from α-form ZnPc nanowire seems to be attributed to the change of electronic energy state of ZnPc upon its self-assembly via π-π stacking. As briefly mentioned, monomeric of ZnPc has PD activity due to its long-lived triplet states. However, the stacking of ZnPc molecules via π-π interaction causes transfer of the triplet excitation energy, resulting in a shortened triplet state lifetime together with an increased probability of non-radiative relaxation. The Q-band broadening in α-form ZnPc nanowire is also attributed to π-π interactions among Pc rings.

Moreover, as shown in FIGS. 18 to 22, the temperature of the α-form ZnPc nanowire solution increased upon laser irradiation from room temperature to about 40° C., which is proportional to the concentration, and the increase in the temperature was similar to that in the ZnPcS$_4$ solution. When laser irradiation at 808 nm was used, however, only the α-form ZnPc nanowire solution (120 mg/L) showed the increase temperature up to 46° C., whereas the ZnPcS$^4$ solution showed negligible temperature changes.

Experimental Example 4

Synergic Phototherapy of Cancer Using α-Form ZnPc Nanowires

1. Experiments for Caner Phototherapy of α-Form ZnPc Nanowires

The α-form ZnPc nanowire solution was examined for cellular uptake and synergic phototherapy of cancer. The α-form ZnPc nanowire solution was treated with human epidermoid mouth carcinoma KB cells to examine its cellular uptake. Confocal micro-Raman spectroscopy was used to track ZnPc nanowires in the cells using both spectroscopy and imaging modes.

As ZnPc shows characteristic Raman bands at 1336, 1506 cm$^{-1}$ corresponding to pyrrole stretching modes, the intracellular internalization of α-form ZnPc nanowires was directly identified by confocal Raman spectroscopy. Human epidermoid mouth carcinoma KB cells (Korean Cell Line Bank) were cultured in RPMI 1640 medium supplemented with 10% fetal bovine serum (FBS) and 1% penicillin/streptomycin at 37° C. in a humidified atmosphere with 5% CO$_2$. The KB cells were seeded on a glass cover slip in 24-well plates for 18 hours at a density of 1×10$^5$ cells per well in 1 ml of medium. The medium was replaced with fresh media and the cells were incubated with 50 mg/L ZnPc nanowires (prepared in Example 1) for 12 hours at 37° C. under 5% CO$_2$ atmosphere. After incubation, the cells were thoroughly rinsed with phosphate buffer saline (PBS), then a cell-seeded cover slip was placed on a glass slide for the measurements. The pyrrole stretching band was measured using a Raman spectrometer (laser excitation wavelength of 532 nm, 3 mW power, 100× objective, 0.3 s integration time, confocal mode, Alpha 300R, Witec). Raman mapping images were collected at 2 μm intervals.

The obtained results are shown in FIGS. 23 to 25.

FIG. 23 shows characteristic Raman spectra of as-grown α-form ZnPc nanowire and its aqueous solution. Both Raman spectra exhibited distinct pyrrole stretching bands at 1336 and 1506 cm$^{-1}$ (FIG. 23). After incubating KB cells in α-form ZnPc nanowire solution (50 mg/L) for 12 hours, the cells showed both pyrrole stretching bands, while both bands were completely absent from the untreated cells (FIG. 24). The confocal spectral images mapped with both bands ((a) and (b) in FIG. 25) confirmed that α-form ZnPc nanowires were not adsorbed on the cell surface, but certainly uptaken into the cells (FIG. 25).

2. Measurement of Phototherapeutic Effect of α-Form ZnPc Nanowires

The synergic phototherapeutic effect of α-form ZnPc nanowires on cancer-cell destruction was studied by culturing KB cells with α-form ZnPc nanowire solution and measuring the cell viability using a colorimetric MTS assay Pre-incubated human KB cells (0.5×10$^5$ cells/ml) were incubated with α-form ZnPc nanowire solution (120 mg/L) for 18 hours at 37° C. with 5% CO$_2$. After incubation, cells were rinsed with PBS followed by irradiation with an 808 nm laser at 3 W/cm$^2$ for 5 minutes. Trypan blue was used to stain the dead cells. Cell viability was determined by CellTiter A96 (Promega) assay. Each cell sample was treated with tetrazolium compound (3-(4,5-dimethylthiazol-2-yl)-5-(3-carboxymethoxyphenyl)-2-(4-sulfophenyl)-2H-tetrazolium, inner salt; MTS) and electron coupling reagent (phenazine methosulfate; PMS) and incubated for 2 hours at 37° C. with 5% CO$_2$. Absorbance at 490 nm was measured to determine the concentration of formazan, which was bioreduced from MTS by metabolically active and viable cells.

The obtained results are shown in FIGS. 26 and 27.

As shown in FIGS. 26 and 27, while the untreated cells and only the cells treated with α-form ZnPc nanowires showed high viability (FIG. 26 top), the cells treated with α-form ZnPc nanowires followed by NIR (λ=808 nm) illumination were stained with trypan blue indicating cell destruction (FIG. 26 bottom left). After 24 hours of the treatment, the cell destruction was more obvious (FIG. 26 bottom right). The cells treated with α-form ZnPc nanowires and NIR initially generated some bubbles around the cell surface (FIG. 26 bottom left). This phenomenon implies that cells are oxidatively damaged, which is similar to the case when the cells are treated with H$_2$O$_2$. The statistical data indicates that the viability of the cells treated with α-form ZnPc nanowires and NIR decreases more than 50% compared with the untreated one, which is lower than other parallel sets of control groups, including the cells treated with ZnPcS$_4$ and NIR (FIG. 27).

3. Measurement of Phototherapeutic Efficacy of α-Form ZnPc Nanowires Using Tumor-Bearing Mouse Model On the basis of the above experimental results, the in vivo experiments were performed to evaluate phototherapeutic efficacy of α-form ZnPc nanowires using a tumor-bearing mouse model.

Specifically, the KB cells (1×10$^7$ cells) were inoculated into the back of male BALB/c mice (n=4, 5- to 6-week-old).

When the tumor volume reached approximately 70 mm³, the mice were intratumorally injected with α-form ZnPc nanowire solution (100 μl, 120 mg/L) and immediately irradiated with an 808 nm laser (3 W/cm², 3 minutes) under ether anesthesia. The tumor size was measured every 3 days. All procedures for in vivo experiments were performed in accordance with the Pohang University of Science and Technology guidelines on animal care and use.

The experimental setup is shown in FIG. 28. When the tumor size reached approximately 70 mm³ (FIG. 28 top), α-form ZnPc nanowire solution was introduced to the tumor region via intratumoral injection, then immediately illuminated with the same NIR laser (808 nm) at a power density of 3 W/cm² for 3 minutes (FIG. 28 middle).

The tumor growth rates measured from different treatment groups are shown in FIG. 29.

As shown in FIG. 29, the solid tumor was completely eradicated from the mouse treated with both α-form ZnPc nanowires and NIR (FIG. 28 bottom and FIG. 28 triangle), whereas all other control groups showed continuous growth of tumor. The reliability of the phototherapeutic effect of α-form ZnPc nanowires was confirmed by observing similar reproducible results from four different batches.

Moreover, the damage to tumor tissue was further confirmed by histological assessment. Mice were euthanized 12 hours after all treatment, and tumor tissues of each group were resected and fixed overnight in 4% paraformaldehyde solution. Tumor tissues were then embedded in paraffin after tissue processing. Paraffin sections were mounted on a glass slide for histological assessment with hematoxylin and eosin (H&E) staining, and with terminal deoxynucleotidyl transferase biotin-dUTP nick-end labeling (TUNEL assay, Calbiochem) to detect apoptotic or necrotic cells.

The obtained results are shown in FIG. 30.

Moreover, as shown in FIG. 30, the hematoxylin and eosin (H&E) staining results reveal the characteristics of dead cells, such as cell shrinkages, nucleus loss and considerable karyolysis in the tumor tissue treated with α-form ZnPc nanowires and NIR (FIG. 30 part A). Furthermore, the TUNEL assay, identifying necrotic or apoptotic cells, exhibits obvious brown color from most parts of the cell treated with α-form ZnPc nanowires and NIR, which indicates extensive cell death (FIG. 30). On the other hand, other control groups show robust and viable tumor cells remained.

Example 2

Preparation of Composites of α-Form Zinc-Phthalocyanine Nanowire/Phenothiazine

Through a solid-vapor transport reaction, called the vaporization-condensation-recrystallization (VCR) process, using ZnPc powder and phenothiazine as precursors, composites of α-form zinc-phthalocyanine nanowire/phenothiazine were prepared.

Specifically, ZnPc powder (0.05 g, Sigma-Aldrich) and phenothiazine (0.03 g, Sigma-Aldrich) were loaded in a ceramic boat, which was located at the center of a quartz tube placed in an electrical heating furnace system. Before the reaction, the quartz tube was flushed with Ar gas at a flow rate of 800 sccm for 5 minutes to remove trapped ambient gases and then heated up to 550° C. under steady Ar flow. A Si(100) substrate (wafer, WRS materials) was placed at the end region (downstream) of the furnace.

During the reaction, the ZnPc powder and phenothiazine placed at the center of a tube-type hating furnace were vaporized at 550° C., and ZnPc vapors and phenothiazine vapors were delivered by Ar gas downstream where the Si wafer was located. The ZnPc vapors were condensed on the Si wafer as the substrate temperature was naturally lowered to 180° C., at which one-dimensional composites of ZnPc nanowire/phenothiazine grow. The reaction was maintained for 40 minutes for the growth of composites of ZnPc nanowire/phenothiazine and then the sample was cooled to room temperature under Ar flow.

FIG. 31 shows the composite of α-form zinc-phthalocyanine nanowire/phenothiazine, in which part (a) shows the molecular structure of phenothiazine, part (b) shows an image of phenothiazine nanowire prepared on a Si substrate by the VCR process, and an optical microscope image and a fluorescence microscopy image of nanowire structure, and part (c) shows the outline of the VCR process and an image of a zinc-phthalocyanine/phenothiazine composite prepared on the Si substrate.

As shown in FIG. 31, the composite of α-form zinc-phthalocyanine nanowire/phenothiazine was shown in blue in part (c), and phenothiazine nanowires shown in white in part (b), from which it can be seen that they are shown in different colors.

Experimental Example 5

Analysis of Structural Changes of Composite of α-Form Zinc-Phthalocyanine Nanowire/Phenothiazine The scanning electron microscopy (SEM) was used to analyze the structural changes of the composites in which their colors differ depending on the position of Si substrate. The results of the SEM analysis are shown in FIG. 32.

As shown in FIG. 32, it was found that the composite of α-form zinc-phthalocyanine nanowire/phenothiazine was in the form of nanowires, and nanowires and two-dimensional structures were simultaneously produced at position C.

Experimental Example 6

Determination of Fluorescence of Composites of α-Form Zinc-Phthalocyanine Nanowire/Phenothiazine A solution was prepared by placing a portion containing only nanowires, isolated from the composites of α-form zinc-phthalocyanine nanowire/phenothiazine, into distilled water, followed by sonication. Moreover, to determine whether the fluorescence observed in phenothiazine could also be observed in the composite, the phenothiazine nanowire solution, α-form zinc-phthalocyanine nanowire solution, and composite solution of α-form zinc-phtalocyanine nanowire/phenothiazine were irradiated with ultraviolet light, respectively. Fluorescence images of the respective solutions when exposed to light at a wavelength of 365 nm are shown in part (a) of FIG. 33, and fluorescence spectra of the phenothiazine nanowire solution, α-form zinc-phthalocyanine nanowire solution, and composite solution of α-form zinc-phtalocyanine nanowire/phenothiazine at a wavelength of 340 nm are shown in part (b) of FIG. 33.

As shown in part (a) of FIG. 33, it was found that the fluorescence was observed in the composite solution of α-form zinc-phtalocyanine nanowire/phenothiazine, but not observed in the α-form zinc-phtalocyanine nanowire solution.

Moreover, as shown in part (b) of FIG. 33, it was found that the fluorescence peak was observed at 450 nm in the composite solution of α-form zinc-phtalocyanine nanowire/phenothiazine through the fluorescence spectra obtained when a wavelength of 340 nm was irradiated onto the three solutions.

As described above, the one-dimensional ZnPc nanowires grown from ZnPc powder by the VCR process have α-form crystal structure and exhibit increased dispersibility in water. The increased water dispersibility of α-form ZnPc nanowire attributes to its crystal structure providing increased changes for water to interact more with ZnPc nanowire over β-form ZnPc powder through hydrogen bonding (H of water to N) and coordination of water to Zn(II). Although the original ZnPc photosensitizer has only a PD property, ZnPc nanowire exhibits dual PD and PT properties, as both in vitro and in vivo phototherapeutic experiments against KB cancer cells demonstrate successful eradication of cancer cells.

As a result, the growth of ZnPc powder into nanowires has proven that it is possible to solve the intrinsic problem of low water solubility and improve the properties for dual PD and PT effects.

Moreover, with the preparation of the composite of α-form zinc-phthalocyanine nanowire/phenothiazine, it is possible to overcome the drawback that the introduction into the fluorescence imaging system is not easy due to the absence of fluorescence, and thus the diagnosis and treatment can be achieved at the same time using a single substance.

Next, Preparation Examples of the pharmaceutical composition of the present invention will be suggested.

Preparation Examples

Preparation of Pharmaceutical Compositions

1. Preparation of Powders

| | |
|---|---|
| α-form zinc-phthalocyanine nanowires or composite of α-form zinc-phthalocyanine nanowire/phenothiazine: | 200 mg |
| Lactose: | 100 mg |

The above ingredients are mixed and packed in airtight bags to prepare powders.

2. Preparation of Tables

| | |
|---|---|
| α-form zinc-phthalocyanine nanowires or composite of α-form zinc-phthalocyanine nanowire/phenothiazine: | 200 mg |
| Corn starch: | 100 mg |
| Lactose: | 100 mg |
| Magnesium stearate: | 2 mg |

The above ingredients are mixed and compressed into tablets according to a conventional method for preparing tables.

3. Preparation of Capsules

| | |
|---|---|
| α-form zinc-phthalocyanine nanowires or composite of α-form zinc-phthalocyanine nanowire/phenothiazine: | 200 mg |
| Corn starch: | 100 mg |
| Lactose: | 100 mg |
| Magnesium stearate: | 2 mg |

The above ingredients are mixed and filled in gelatin capsules to prepare according to a conventional method for preparing capsules.

4. Preparation of Injections

| | |
|---|---|
| α-form zinc-phthalocyanine nanowires or composite of α-form zinc-phthalocyanine nanowire/phenothiazine: | 200 mg |
| Mannitol: | 100 mg |
| $Na_2HPO_4 \cdot 12H_2O$: | 2 mg |
| Sterile distilled water for injection: | Suitable amount |

Injections are prepared with the above ingredients per ampoule (2 ml) according to a conventional method for preparing injections.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

The invention claimed is:

1. A method comprising preparing nanowires comprising α-form zinc-phthalocyanine, wherein the α-form zinc-phthalocyanine is represented by Formula 1, wherein the preparing nanowires comprises:
   (a) generating zinc-phthalocyanine (ZnPc) vapor by vaporizing zinc-phthalocyanine at a first temperature from 500 to 1,000° C. under a first inert gas atmosphere; and
   (b) forming the nanowires by condensing and recrystallizing the zinc-phthalocyanine vapor at a second temperature from room temperature to 300° C. under a second inert gas atmosphere:

[Formula 1]

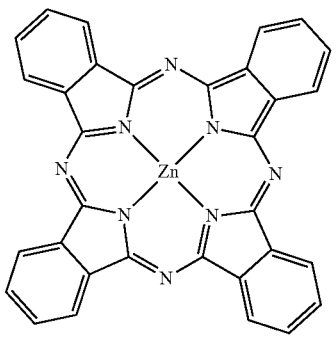

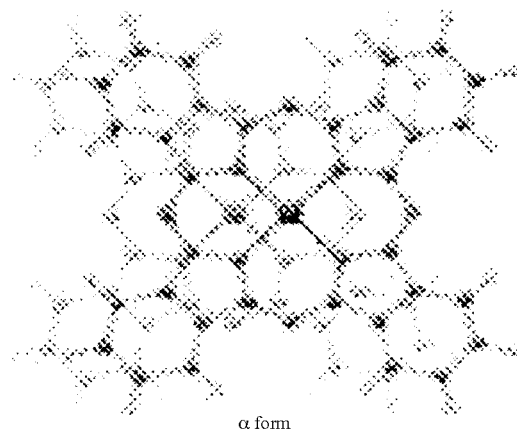

α form

2. The method of claim 1, wherein the nanowires are formed on a substrate.

3. The method of claim 2, wherein the temperature of the substrate is from room temperature to 180° C.

4. The method of claim 1, wherein the first or second inert gas atmosphere comprises nitrogen, argon, or helium.

* * * * *